US006529876B1

United States Patent
Dart et al.

(10) Patent No.: US 6,529,876 B1
(45) Date of Patent: Mar. 4, 2003

(54) ELECTRONIC TEMPLATE MEDICAL RECORDS CODING SYSTEM

(76) Inventors: Stephen H. Dart, P.O. Box 387, Richland, WA (US) 99352; Neil W. Rawlins, 1131 Saddle Way, Richland, WA (US) 99352

( * ) Notice: Subject to any disclaimer, the term of this patent is extended or adjusted under 35 U.S.C. 154(b) by 0 days.

(21) Appl. No.: 09/277,857

(22) Filed: Mar. 26, 1999

(51) Int. Cl.[7] ............................................. G06F 17/60
(52) U.S. Cl. .............................................. 705/4; 705/2
(58) Field of Search .................................. 705/2, 3, 4

(56) References Cited

U.S. PATENT DOCUMENTS

| | | | | |
|---|---|---|---|---|
| 5,483,443 A | * | 1/1996 | Milstein et al. ................ | 705/4 |
| 5,583,758 A | * | 12/1996 | McIlroy et al. ................ | 705/4 |
| 5,924,074 A | * | 7/1999 | Evans ........................... | 705/3 |
| 5,953,704 A | * | 9/1999 | McIlroy et al. ................ | 705/2 |

FOREIGN PATENT DOCUMENTS

JP 08248453 * 5/1997

OTHER PUBLICATIONS

A Blueprint For Documenting Your E&M Services, Conomikes Medicare Hotline, Nov. 1997, vol. 7, No. 1 Conomikes Associates, Inc.

St. Anthony's Guide to Evaluation and Management Coding and Documentation, Third Edition, St. Anthony Publishing, Inc. 1998, pp. TOC–1—3–5.

Physicians' Current Procedural Terminology CPT' 98 Prof. Edition. American Medical Assn., 1998, pp. 1–8.

* cited by examiner

Primary Examiner—Sam Rimell
(74) Attorney, Agent, or Firm—Liebler, Ivey & Connor; Floyd E. Ivey

(57) ABSTRACT

A method and a computer program and computer apparatus for use by health care providers for the production of accurate billing coding for care rendered. The invention established the process, the data gathering and documentation required of a provider in determining and documenting correct Evaluation and Management CPT code(E&M code or E&M coding) required for agency reimbursement for care delivered. This invention is directed to a computer and computer program wherein a computer program requires a computer to perform a complete audit of E&M coding prior to billing thus ensuring compliance with statutory and regulatory requirements. The system enables providers to comply with statutory and regulatory reporting requirements demonstrating the meeting of Federal and State statutory and regulatory standards prerequisite to payment to the medical provider for health care delivered.

10 Claims, 10 Drawing Sheets

Prior Art Coding Process    Figure 1
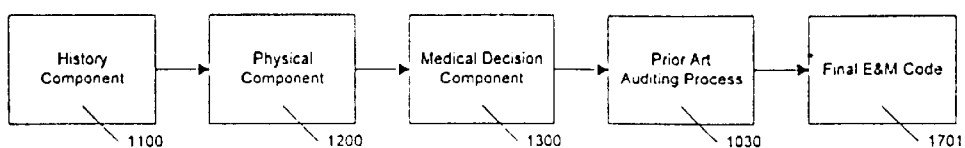
Figure 2
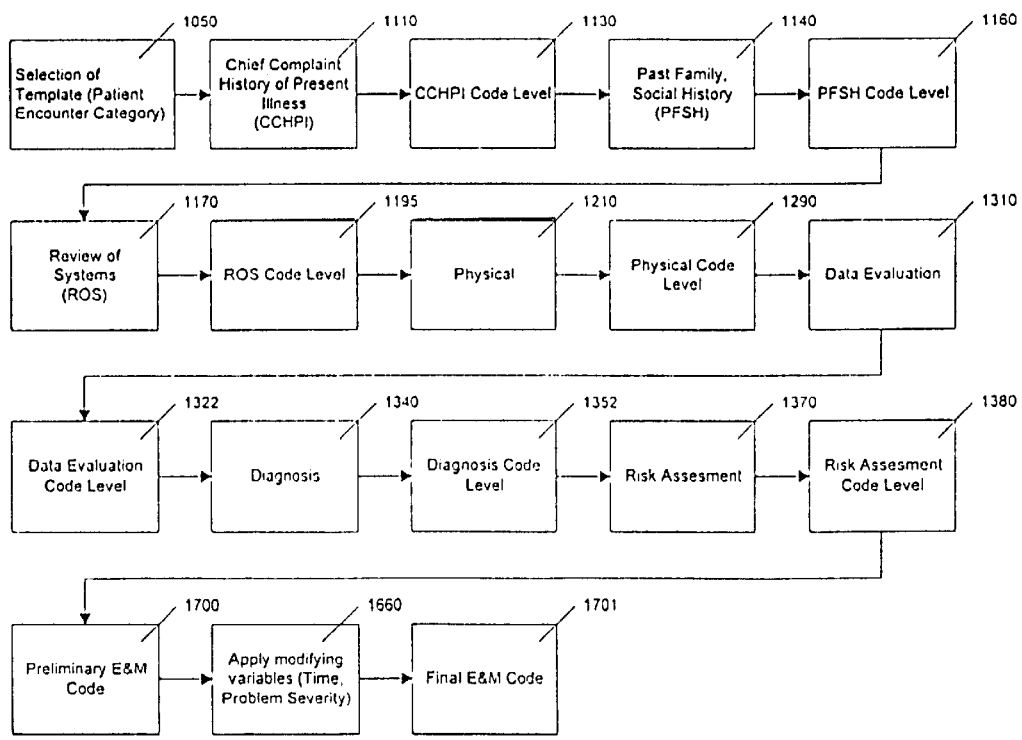

Used to determine Comprehensive (Level 5) for Coding

Figure 8

| | | Const 2 each from 9 Systems | Eye | Head / Face | E, N, M. & T | Neck | Resp | Cardio | Chest/ Breasts | Gastro | Genito Abdomen | Lymph | Musculo | Extrem | Skin | Neuro/ Psych |
|---|---|---|---|---|---|---|---|---|---|---|---|---|---|---|---|---|
| General Exam | | Subset (3 of 7) | X | X | X | X | X | X | X | X | X | Subset (2 of 4) | Subset (3 of 8) | X | X | X |
| Cardiovascular Exam | All Elements | | | | | X | X | X | | X | | | | | | X |
| | One Each | | X | X | X | X | | | | | | | X | X | X | |
| | Subset | X | | | | | | | | | | | | | | |
| Ear, Nose, Throat Exam | All Elements | | | X | X | X | X | X | | | | | | | | X |
| | One Each | | X | | | | | | | | | X | | | | |
| | Subset | X | | | | | | | | | | | | | | |
| Eye Exam | All Elements | | X | | | | | | | | | | | | | |
| | One Each | | | | | | | | | | | | | | | X |
| Genitourinary Exam | All Elements | | | | | | | | | | X | | | | X | X |
| | One Each | | | | X | X | X | | | | | X | | | | |
| | Subset | X | | | | | | | | | X | | | | | |
| Hematologic / Lymphatic /Immunologic Exam | All Elements | | | | | | | | | X | | | | | | X |
| | One Each | | X | X | X | X | | | | | | X | | X | X | |
| | Subset | X | | | | | | | | | | | | | | |
| Musculoskeletal Exam | All Elements | | | | | | | | | | | | | X | | X |
| | One Each | X | | | | | | | | | | X | X | | X | |
| | Subset | | | | | | | | | | | | | | | |
| Neurological Exam | All Elements | | X | | | | | X | | | | | | | | X |
| | One Each | | | | | | | | | | | | | | | |
| | Subset | X | | | | | | | | | | | | | | |
| Respiratory Exam | All Elements | | | | X | X | X | X | | X | | | | | | X |
| | One Each | | | X | | | | | | | | X | X | X | X | |
| | Subset | X | | | | | | | | | | | | | | |
| Skin Exam | All Elements | | | | X | | | | | | | | | | | X |
| | One Each | | X | | | | | X | | X | | X | | X | X | |
| | Subset | X | | | | | | | | | | | | | | |
| Psychiatric Exam | All Elements | | | | | | | | | | | | | | | |
| | One Each | | | | | | | | | | | | X | X | X | |
| | Subset | X | | | | | | | | | | | | | | |

All Elements means documentation required all elements in each System / Body area.
One Each means documentation required at least one element in each System / Body area.
Subset means documentation required a defined subset of elements in each System / Body area.

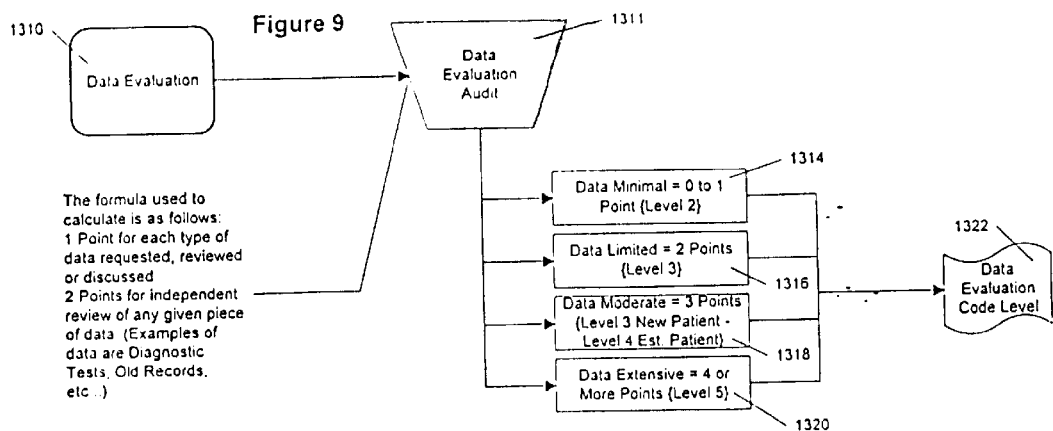
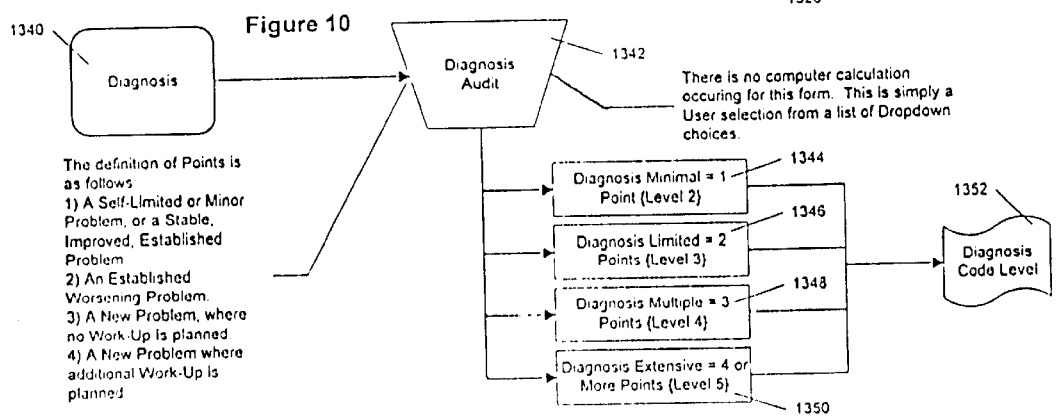
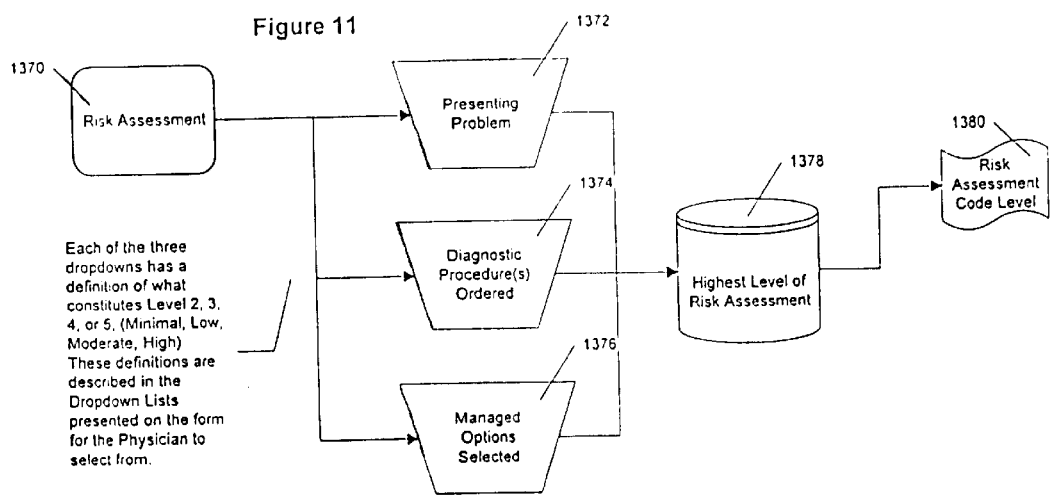

ELECTRONIC TEMPLATE MEDICAL RECORDS CODING SYSTEM

FIELD OF THE INVENTION

The present invention relates generally to a method and apparatus for electronic coding of medical services rendered to patients and particularly to a method of coding medical services rendered to patients for compliance with Federal and State statutory and regulatory requirements for the avoidance of fraud and abuse in application for reimbursement from governmental agencies for services rendered pursuant to regulations including Health Care Financing, Medicare and Department of Health and Human Services regulations.

BACKGROUND OF THE INVENTION

Medical providers are eligible for the receipt of payments from governmental agencies upon providing certain care. Providers are required by statute and regulation to meet particular standards, in reporting and requesting payment, for the purpose of avoiding the commitment of fraud and abuse in requesting and receiving such payment. The provider must properly and correctly code multiple aspects of an encounter with a patient to form the basis for meeting regulatory requirements required for payment. Incorrect coding may likely result in noncompliance with laws or regulations such as the Federal False Claims Act (31 USC 3729), the Health Insurance Portability and Accountability Act (HIPAA), Stark I and II and similar Federal and State laws enacted to protect against fraudulent claims for reimbursement for the providing of health care. Medical providers are thus exposed to criminal and civil penalties relating to compliance with regulatory and statutory requirements.

The medical encounter documentation and coding is increasingly complex. Health Care Financing and Medicare rules require documentation of multiple items for every patient seen. For example, there are likely at least 20 items to be documented for each patient encounter and now, for some care, more than 85 items to be documented.. It is ever more difficult for the provider to remember all of the necessary individual documentation items and to document them appropriately. Increases in staffing has been recommended as a means of addressing the burden of correct coding to insure the submission of reimbursement requests which comply with regulatory requirements. However, steps directed to accurate pre-billing audits have left the human element in place and leaving the provider with the difficult burden of correctly and accurately recalling and interrelating each item required to be documented for each patient. The provider is required to expend additional time, remain exposed to the hazard of forgetting an item for the patient and being subjected to civil and criminal sanctions as well as experiencing the increased cost associated with the pre-audit process.

Due to the complexity of, potential for error in Evaluation and Management Coding (E&M coding) and the potential severity of penalty for noncompliance, many providers deliberately under-code patient encounters resulting in a loss of revenue to the provider. Some estimate that as many as 80% of providers under-code from fear of unintentional noncompliance and resulting legal action. Guides exist for use by providers including "A Blueprint For Documenting Your E&M Services", Conomikes Medicare Hotline, November 1997, Vol. 7, Number 1 revised 1998 and St. Anthony's "Guide to Evaluation and Management Coding and Documentation", Third Edition. Disclosures are provided herewith in an Information Disclosure Statement in accordance with 37 CFR 1.97.

SUMMARY OF THE INVENTION

The preferred embodiment of the invention provides a method and apparatus to maximize efficiency and accuracy for the provider in determining and documenting correct Evaluation and Management CPT code(E&M code or E&M coding) as required for agency reimbursement for health care delivered. Evaluation and Management (E&M) services are divided into broad categories such as office visits, hospital visits, and consultations. Most of the categories are further divided into two or more subcategories of E&M services. There are two subcategories of office visits including new and established patient and two subcategories of hospital visits including initial and subsequent. The subcategories of E&M services are further classified into levels of E&M services that are identified by specific codes. This classification is important because the nature of physician work varies by type of service, place of service and the patient's status. The basic format of the levels of E&M services is the same for most categories. First, a unique code number is listed. Second, the place and or type of service is specified, for example, office consultation. Third, the content of the service is defined, for example, comprehensive history and comprehensive examination. Fourth, the nature of the presenting problem(s) usually associated with a given level is described. Fifth, the time typically required to provide the service is specified. The levels of E&M services include examinations, evaluations, treatments, conferences with or concerning patients, preventive pediatric and adult health supervision, and similar medical services, such as the determination of the need and or location for appropriate care. Medical screening includes the history, examination, and medical decision-making required to determine the need and or location for appropriate care and treatment of the patient. The levels of E&M services encompass the wide variations in skill, effort, time, responsibility and medical knowledge required for the prevention or diagnosis and treatment of illness or injury and the promotion of optimal health. Each level of E&M services may be used by all medical care providers for the generation of an E&M code representing the level of E&M services rendered for each patient encounter.

This method and apparatus is directed to an electronic or computer base wherein a computer directed by a computer program performs a complete audit of E&M coding prior to billing thus ensuring compliance with statutory and regulatory requirements. The present invention prompts the provider to acquire and document data specifically required for the medical evaluation and, ultimately, the billing for professional services for each different type of patient encounter. The invention effectuates the provider's actions necessary to meet audit requirements. The present invention is therefore a highly effective system in effecting the required bilateral interaction of the provider with both the patient and the E&M coding requirements of each specific type of patient encounter.

The preferred embodiment of the present invention is the establishment of a unique electronic exam template for each specific type of E&M service or patient encounter. The unique template prompts the provider in the acquisition of data peculiar to the specific type of patient encounter as dictated both by standards of medical care and as required by statutory and regulatory standards of E&M code requirements for billing and reporting to regulatory agencies. The preferred embodiment of the invention is the method of use of the electronic exam template as the basic user interface component of the system. A template or form, specific to the particular type of patient encounter, is displayed on a computer screen which contains text fields, drop-down lists, check boxes and graphics. An exam builder utility provides the capabilities necessary to define a dynamic rules base necessary to automatically code the correct E&M code appropriate for the patient encounter. This E&M code is used for billing purposes and directly affects the physician reimbursements from insurance and managed care organizations.

In one embodiment of this invention, the provider, by use of exam builder utility programs, can produce exam templates having characteristics relating to that provider's specific medical practice or preferences.

An exam template is comprised of a logical related set of systems. These systems are created with the exam builder utility allowing the provider to create a set of questions and response areas to cover a specific subject matter. These systems are then combined into a group and saved as an exam template. A system is a related set of questions covering a given subject area. These questions are created as system items. Each system item has a set of attributes which define the question, the type of data to gather, the placement on the form, whether it is part of a regulatory requirement for billing and reimbursement purposes and other attributes. The provider is prompted by the exam template to acquire data in order to answer the appropriate set of questions and to address the appropriate response areas required by the specific patient circumstance. The answers and responses of the provider create data input which is processed by the computer, responding to the computer program, to produce an E&M code compliant with the regulatory requirements prerequisite to billing for services rendered.

A relational model is used to store the template and item components of the template medical coding system. The system allows for reuse of a system across multiple Exam Templates. It also provides for complete documentation of the encounter with the patient. There is a consistency of questioning across patients. This consistency provides for more audit friendly records in terms of documentation and coding. The primary benefit of this design however lies in its ability to allow for creation of what is herein referred to as a Rules Base. The Rules Base reference is to the audit rules established by statutory and regulatory requirements previously addressed herein.

The E&M coding process consists primarily of counting questions of certain types and following a number of decision trees. The path taken in these decision trees is based on the questions asked and number of questions answered for each types of patient encounter. The problem the provider has is determining what has and has not been covered with the patient. The provider, using the prior art, must determine by hand the results of the exam in terms of how many Rules Based questions have been addressed; the provider must then remember how they play out in terms of the decision trees. The Rules Base concept supported by the template system here disclosed enables, by computer program, the provider to enter data and the computer then to make these required calculations. A separate Rules Base is defined for each separate type of patient encounter. Each patient encounter will require the provider to complete a History Component, a Physical Component and a Medical Decision Component. Each different type of patient encounter will subject the provider to forming data, regarding each of these components, peculiar to the specific type of patient encounter. For example, the following are indicative of the different types of patient encounters: general multi-system examination; cardiovascular examination; ear, nose and throat examination; eye examination; genitourinary examination; hematologic/lymphatic/immunologic examination; musculoskeletal examination, neurological examination; psychiatric examination; respiratory examination; and skin examination. The provider will, by training, undertake certain data gathering for each patient encounter including the taking of the patient's history, the making of certain measurements, inspections and examinations and the making of certain medical decisions. The provider will order particular tests and will review the results of the tests. The provider may read a report from another provider regarding test results. The provider may perform the test and prepare the report. The Rules Base established by statutory and regulatory requirements subjects the provider to the documentation of the answers, responses, results, and decisions of each phase of the patient encounter leading to the submitting of a bill for the provider's professional services.

This disclosure requires the provider to enter appropriate date, answer appropriate questions, performs an audit regarding the provider's having addressed each element of interest in the patient encounter to the statutory and regulatory schemes and concludes with a E&M coding which meets statutory and regulatory requirements. The provider will select a template appropriate to the type of patient encounter, e.g., a genitourinary examination. The provider will address each item attribute for such a patient encounter and will enter the data required for the ultimate E&M code for billing. The data entered by the provider, in the form of the provider's answer responses to questions presented by each template, is interrogated by the computer program and computer. Those providing such medical services will recognize that the provider's inquiry and action will differ for each separate type of patient encounter and for each separate patient and patient encounter.

The process described is a change from the current approach of practicing physicians. Instead of using concepts such as problem focused, detailed and comprehensive, the E&M coding is broken down to the individual elements for each patient encounter. Each section of the patient encounter, i.e., History Component, Physical Component and Medical Decision Component, is coded individually by the number of elements or items entered as data entry by the provider. These elements or items are then manipulated by a computer program and computer for auditing, during the patient encounter, and at the end of the patient encounter with an E&M code resulting for use with the regulatory process and billing. The advantage of this invention is that it decreases the chance of entry of data which an auditor would deem illegible or inappropriate thus voiding that entry. The invention also allows the provider to do real time auditing of the E&M coding process. This in turn provides greater consistency and accuracy in E&M coding and enables the provider in approaching the 100% compliance demanded by the current laws. This invention is a significant step in reducing the risk of noncompliance with possible attendant civil and criminal penalties. The invention has also been demonstrated in tests to increase the likelihood of E&M coding at the level representative of the care provided for the patient encounter and hence increase the likelihood of reimbursement at levels appropriate to the patient encounter.

This invention is applicable to the clinic setting, outpatient services, hospital observations, consultations, inpatient services, emergency visits, home visits, and other medical evaluations.

BRIEF DESCRIPTION OF THE DRAWINGS

The foregoing and other features and advantages of the present invention will become more readily appreciated as the same become better understood by reference to the following detailed description of the preferred embodiment of the invention when taken in conjunction with the accompanying drawings, wherein:

FIG. 1 illustrates the prior art E&M coding process.

FIG. 2 is a flow chart illustrating the E&M coding process of this invention representing the data gathering of the provider and the formulating of answers and responses forming the data input which is processed by a computer to produce a pre-billing audited E&M code to insure compliance with the regulatory requirements for billing for services rendered. The provider selects the appropriate electronic template or screen at Selection of Template, depending upon the patient encounter category or type of patient encounter. The provider then gathers data required to fulfill the History Component of the E&M coding: this includes determination of the Chief Complaint History of Present Illness(CCHPI), Past Family, Social History(PFSH) and Review of Systems (ROS). The provider than enters data gathered for each of the History Component resulting in the computer generated appropriate E&M code level for each of CCHPI, PFSH and ROS code levels. The provider then undertakes the Physical or Physical Exam and enters the gathered data required to fulfill the Physical Component resulting in the computer generation of the appropriate E&M code level for the Physical Component or Physical code level. The provider then makes the Risk Assessment and enters the gathered data required for the Risk Assessment resulting in the computer generated appropriate E&M code level for Risk Assessment Code Level. A Preliminary E&M code level is then generated. The provider then applies modifying variables including, for example, time and problem severity, with the computer then generating the regulatory appropriate E&M code or Final E&M code.

The Medical Decision Component encompasses the provider's data gathering required for Data Evaluation Audit, Diagnosis Audit and Risk Assessment Audit following data entry, progresses through the computer generated E&M Code for each of Data Evaluation, Diagnosis and Risk Assessment Code Levels to the computer manipulation of each code level to produce the Level of Highest Two Code Levels. Following is the computer manipulation to produce the Medical Decision Code Level. The Medical Decision Component requires provider medical judgment. Automated pull-down guides, similar to those available in standard references including, for example, St. Anthony's Guide to Evaluation and Management Coding and Documentation", third edition, and Conomikes Medicare Hotline, November 1997, Vol. 7, Number 1, are available to assist the provider in making these judgments. Medical judgments include, for example, the judgment of whether the patient encounter is self limiting or a minor problem.

The computer manipulates the inputs of History Code Level, Physical Code Level and Medical Decision Code Level through a Patient Encounter Category decision tree of "Yes" to Lowest of 3 Code Levels or "NO" to Highest Two Code Levels. A Preliminary E&M code is established. The provider's next step is to Apply Modifying Variables such as counseling, coordination of care, nature of presenting problem and time through to the computer manipulation and production of the Final E&M Code intended to be in compliance with regulatory requirements. Where the Patient Encounter is a "new patient" the E&M code is coded to the lowest of the three overall code levels. Where the Patient Encounter is an "existing patient" the E&M code of the highest two of the three overall E&M code levels is determined and finally coded to the lower of the two E&M code levels. Thus, the overall E&M code level is determined.

Figure 4:
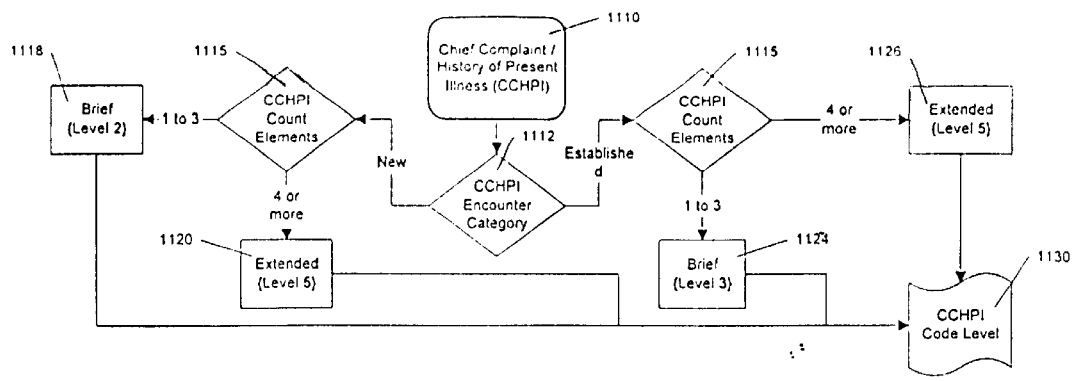

FIG. 4 shows the CCHPI decision tree commencing with the CCHPI Encounter Category to "Established" or to "New". Where to "Established" the tree proceeds to the CCHPI Count Elements with a possible "4 or More" or "1 to 3". Where "4 or more" the progression is to Extended (Level 5); where "1 to 3" the progression is to Brief(Level 3). The final step is the computer generated CCHPI Code Level.

Where to "New" the tree proceeds to the CCHPI Count Elements with a possible "4 or More" or "1 to 3". Where "4 or more" the progression is to Extended(Level 5); where "1 to 3" the progression is to Brief(Level 2). The final step is the computer generated CCHPI Code Level.

Figure 5:
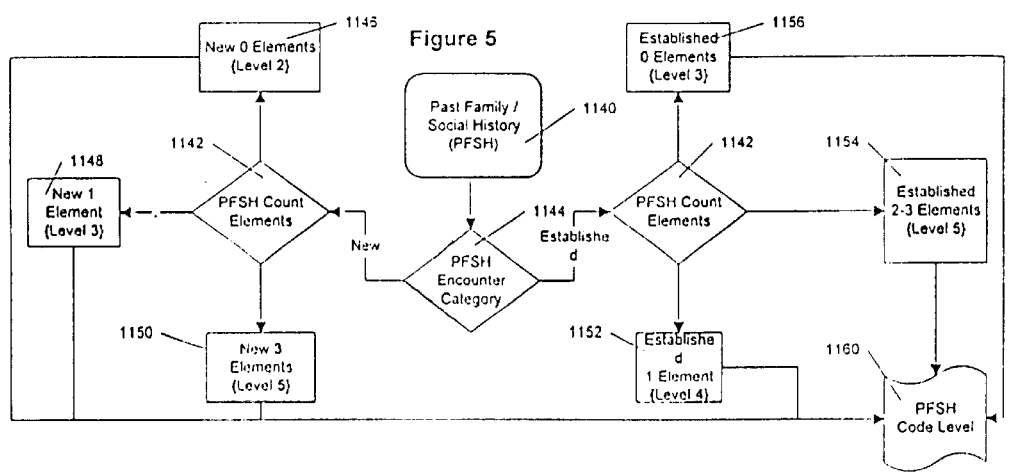

FIG. 5 shows the PFSH decision tree commencing with the PFSH Encounter Category to "Established" or to "New". Where to "Established" the tree proceeds to the PFSH Count Elements with a possible "Established 0 Elements(Level 3)", "Established 1 Element (level 4)" or "Established 2–3 Elements (Level 5)". The progression from each of "Established 0 Elements(Level 3)", "Established 1 Element (level 4)" or "Established 2–3 Elements (Level 5)" is to the computer generation of PFSH Code Level.

Where to "New" the tree proceeds to the PFSH Count Elements with a possible "New 0 Elements(Level 2)", "New 1 Element (level 3)" or "New 3 Elements (Level 5)". The progression from each of "New 0 Elements(Level 2)", "New 1 Element (level 3)" or "New 3 Elements (Level 5)" is to the computer generation of PFSH Code Level.

Figure 6:
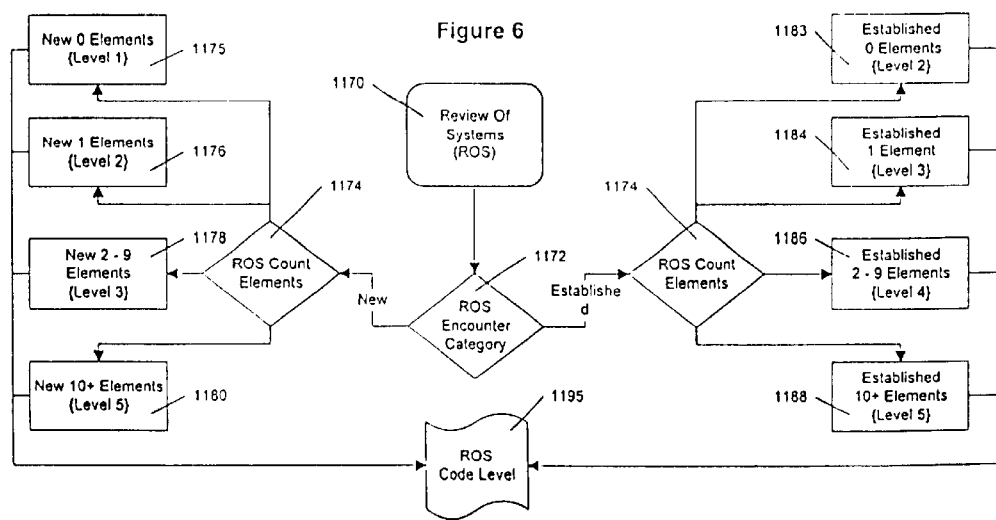

FIG. 6 shows the ROS decision tree commencing with the ROS Encounter Category to "Established" or to "New". Where to "Established" the tree proceeds to the ROS Count Elements with a possible "Established 0 Elements(Level 2)", "Established 1 Element (level 3)", "Established 2–9 Elements (Level 4)" or "Established 10+ Elements (Level 5). The progression from each of "Established 0 Elements (Level 2)", "Established 1 Element (level 3)", "Established 2–9 Elements (Level 4)" or "Established 10+ Elements (Level 5)" is to the computer generation of ROS Code Level.

Where to "New" the tree proceeds to the ROS Count Elements with a possible "New 0 Elements(Level 1)", "New 1 Element (level 2)", "New 2–9 Elements (Level 3)" or "New 10+ Elements(Level 5)". The progression from each of "New 0 Elements(Level 1)", "New 1 Element (level 2)", "New 2–9 Elements (Level 3)" or "New 10+ Elements (Level 5)" is to the computer generation of ROS Code Level.

Figure 7:
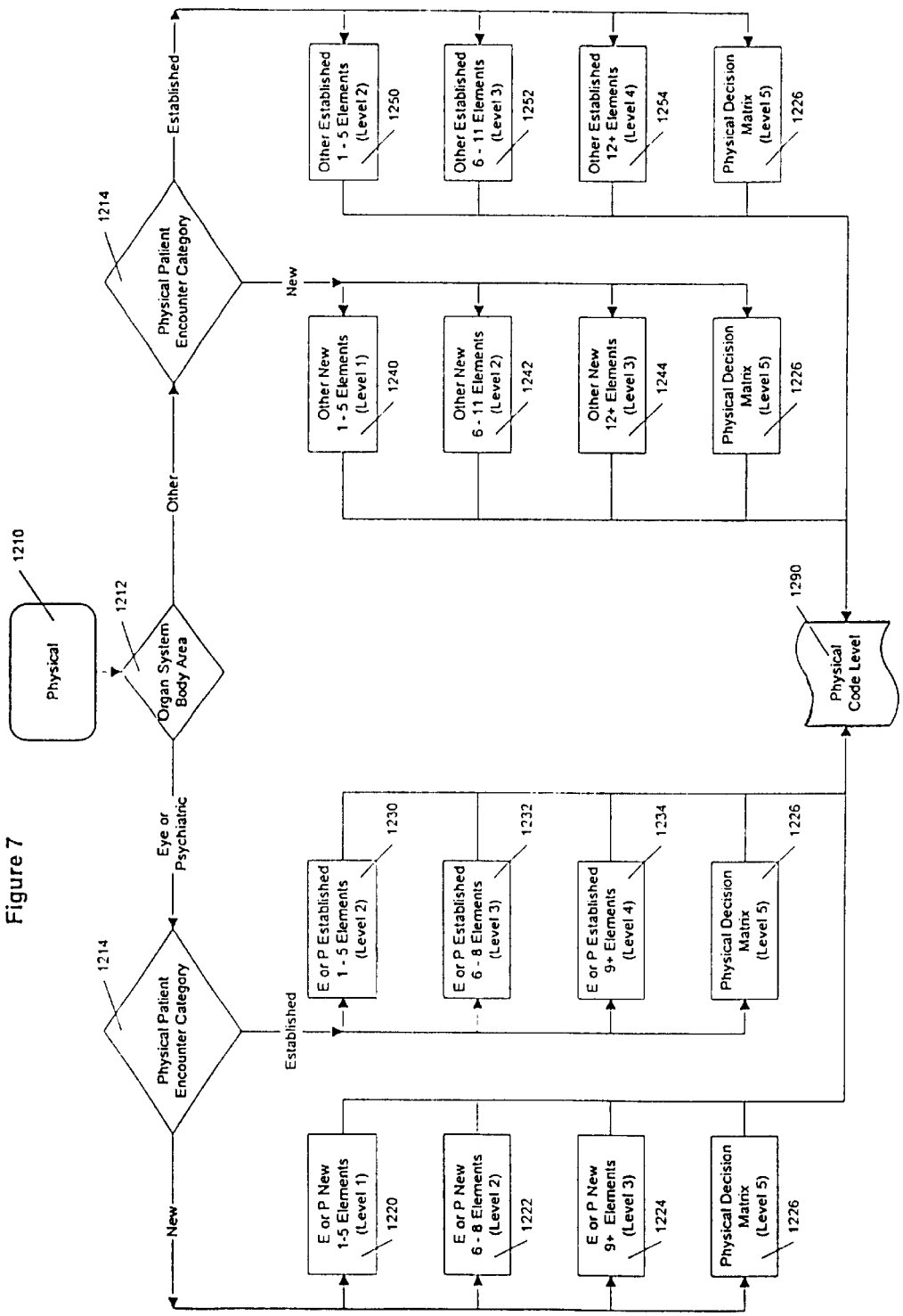

FIG. 7 illustrates the Physical decision tree commencing with the Organ System Body Area to "Other" or to "Eye or Psychiatric". Where to "Other" the tree proceeds to the "Physical Patient Encounter Category" with a possible "Established" or "New". Where "Established" the progression is to "Other Established 1–5 Elements(Level 2)", "Other Established 6–11 Element (level 3)", "Other Established 12+Elements (Level 4)" or "Physical Decision Matrix (Level 5)". The progression from each of "Other Established 1–5 Elements(Level 2)", "Other Established 6–11 Element (level 3)", "Other Established 12+ Elements (Level 4)" or "Physical Decision Matrix (Level 5)" is to the computer generation of Physical Code Level.

Where to "Other", "Physical Patient Encounter Category" and "New" the tree proceeds to the "Other New 1–5 Elements(Level 1)", "Other New 6–11 Elements (level 2)", "Other New 12+ Elements (Level 3)" or "Physical Decision Matrix (Level 5)". The progression from each of "Other New 1–5 Elements(Level 1)", "Other New 6–11 Elements (level 2)", "Other New 12+ Elements (Level 3)" or "Physical Decision Matrix (Level 5)" is to the computer generation of Physical Code Level, Where to "Eye or Psychiatric" the tree proceeds to the "Physical Patient Encounter Category" with a possible "Established" or "New". Where to "Established" the progression is to the "E or P Established 1–5 Elements(Level 2)", "E or P Established 6–8 Elements (level 3)", "E or P Established 9+ Elements (Level 4)" or "Physical Decision Matrix (Level 5)". The progression from each of "E or P Established 1–5 Elements(Level 2)", "E or P Established 6–8 Elements (level 3)", "E or P Established 9+ Elements (Level 4)" or "Physical Decision Matrix (Level 5)" is to the computer generation of Physical Code Level.

Where to "Eye or Psychiatric", "Physical Patient Encounter Category" and "new" the tree proceeds to the "E or P New 1–5 Elements(Level 1)", "E or P New 6–8 Elements (level 2)", "E or P New 9+ Elements (Level 3)" or "Physical Decision Matrix (Level 5)". The progression from each of "E or P New 1–5 Elements(Level 1)", "E or P New 6–8 Elements (level 2)", "E or P New 9+ Elements (Level 3)" or "Physical Decision Matrix (Level 5)" is to the computer generation of Physical Code Level.

FIG. 8 illustrates the physical Decision Matrix. Illustrated is the portion of the Physical Exam that describes the required elements for comprehensive visits. In a comprehensive visit, each subsection has differing numbers of required elements for each of the physical exam templates. Some require all elements; some require only one element; some require subsets of the elements or a specific subset. Examples include:

1. Constitutional: includes a subset of the measurement of "Any three of the following seven vital signs—Sitting or Standing Blood Pressure; Supine Blood Pressure; Pulse Rate and Regularity; Respiration; Temperature; Height;
2. Musculoskeletal System: includes a subset of Examination of joint(s) and muscles(s)/tendon(s) of "four of the following six areas—1) Head and Neck; 2) Spine, Ribs & Pelvis; 3) Right Upper Extremity; 4) Left Upper Extremity; 5) Right Lower Extremity; and 6) Left Lower Extremity."
3. General Multi-System Examination: includes a subset exam of the Lymphatic System which is defined as "two or more of—Neck, Axillae, Groin, Other".
4. Skin Examination: includes a subset defined as "four of the following six—Head & Neck; Trunk; Right Upper Extremity; Left Upper Extremity; Right Lower Extremity; Left Lower Extremity."
5. Genitourinary Examination: includes, if female, a subset defined as "at least Seven of the Eleven" elements relating to females.
6. Skin Examination: includes inspection and/or palpation of skin and subcutaneous tissue in "four of the following five areas- Head and Neck; Chest; Breasts & Back; Abdomen; Genitalia; Extremities."

FIG. 9 shows the Data Evaluation decision tree commencing with the "Data Evaluation Audit" proceeding to the choices of "Data Minimal=0 to 1 Point(Level 2)", "Data Limited=2 Points (Level 3)", "Data Moderate=3 Points (Level 3 New Patient, Level 4 Est. Patient)" or, "Data Extensive=4 or more Points (Level 5)". The progression from each of "Data Minimal=0 to 1 Point(Level 2)", "Data Limited=2 Points (Level 3)", "Data Moderate=3 Points (Level 3 New Patient, Level 4 Est. Patient)" or, "Data Extensive=4 or more Points (Level 5)" is to the computer generation of Data Evaluation Code Level. Also illustrated is the formula used to calculate as follows: 1 Point for each type of data requested, reviewed or discussed; 2 points for independent review of any given piece of data. Examples of data are Diagnostic Tests, Old Records and other items.

FIG. 10 shows the Diagnosis decision tree commencing with the "Diagnosis Audit" proceeding to the choices of "Diagnosis Minimal=1 Point(Level 2)", "Diagnosis Limited=2 Points (Level 3)", "Diagnosis Multiple=3 Points (Level 4)" or, "Diagnosis Extensive=4 or more Points (Level 5)". The progression from each of "Diagnosis Audit" proceeding to the choices of "Diagnosis Minimal=1 Point(Level 2)", "Diagnosis Limited=2 Points (Level 3)", "Diagnosis Multiple=3 Points (Level 4)" or, "Diagnosis Extensive=4 or more Points (Level 5)" is to the computer generation of Diagnosis Code Level. Also illustrated is the definition of Points as follows: 1) A Self-Limited or Minor Problem, or a Stable, Improved, Established Problem; 2) An Established Worsening Problem; 3) A New Problem, where no Work-Up is Planned; 4) A new Problem where additional Work-Up is planned. Also noted is that there is no computer calculation occurring for the Diagnosis Audit with the Diagnosis Audit being simply a User selection from a list of Drop-down Choices.

FIG. 11 shows the Risk Assessment decision tree commencing with the analysis of each of "Presenting Problem", "Diagnostic Procedure(s) Ordered", and "Managed Options Selected" with the following computer examination for the Highest Level of Risk Assessment and progressing to the computer determination of the Risk Assessment Code Level.

Figure 12:
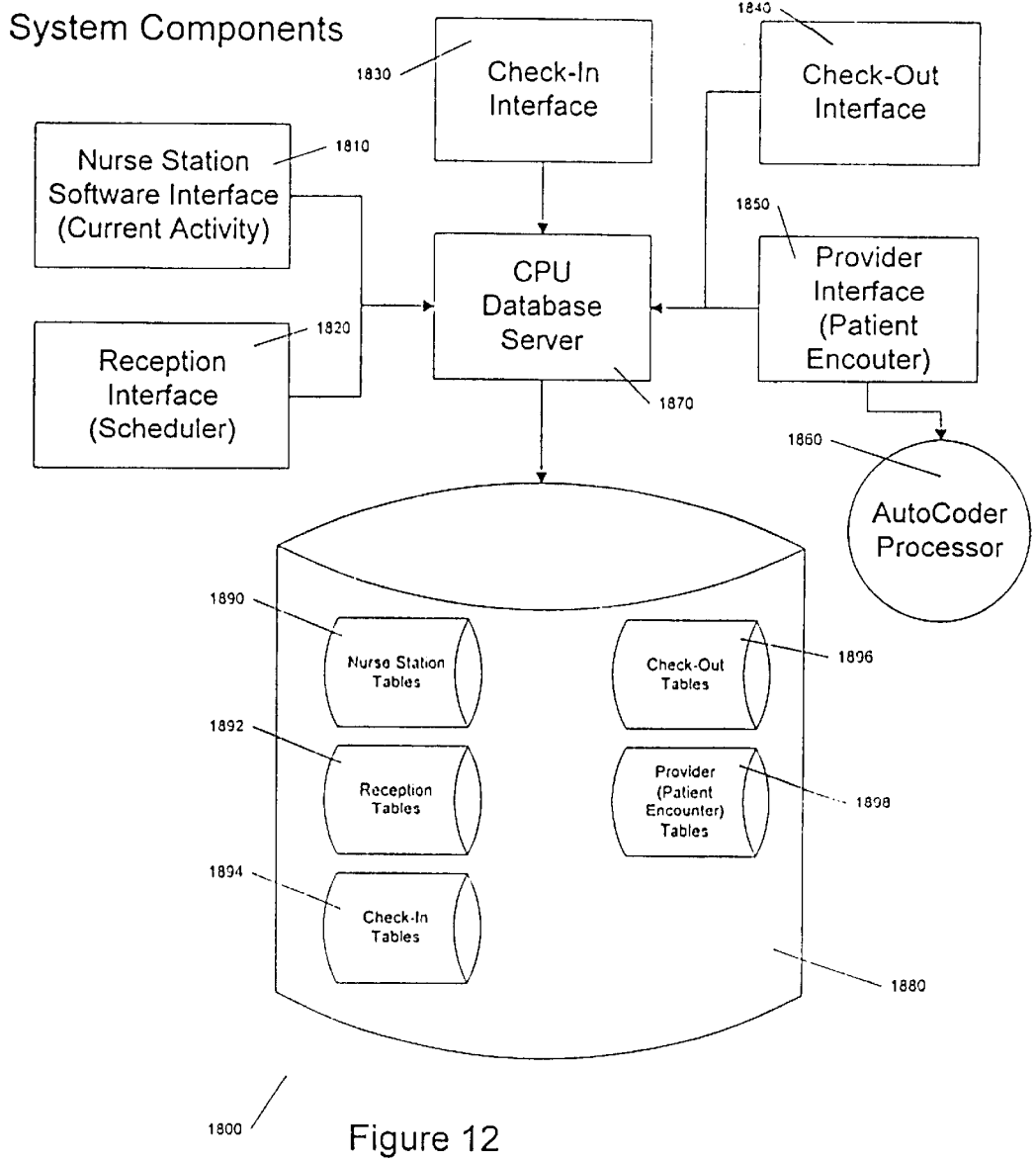

FIG. 12 illustrates the system computer and computer program components showing data entry or personal computer stations including, for example, reception/scheduling, check-in, nurse station, provider interface, checkout interface, and the interconnection with a central processing unit or server computer. The storage for the various data entry or personal computer stations is illustrated.

Figure 13:
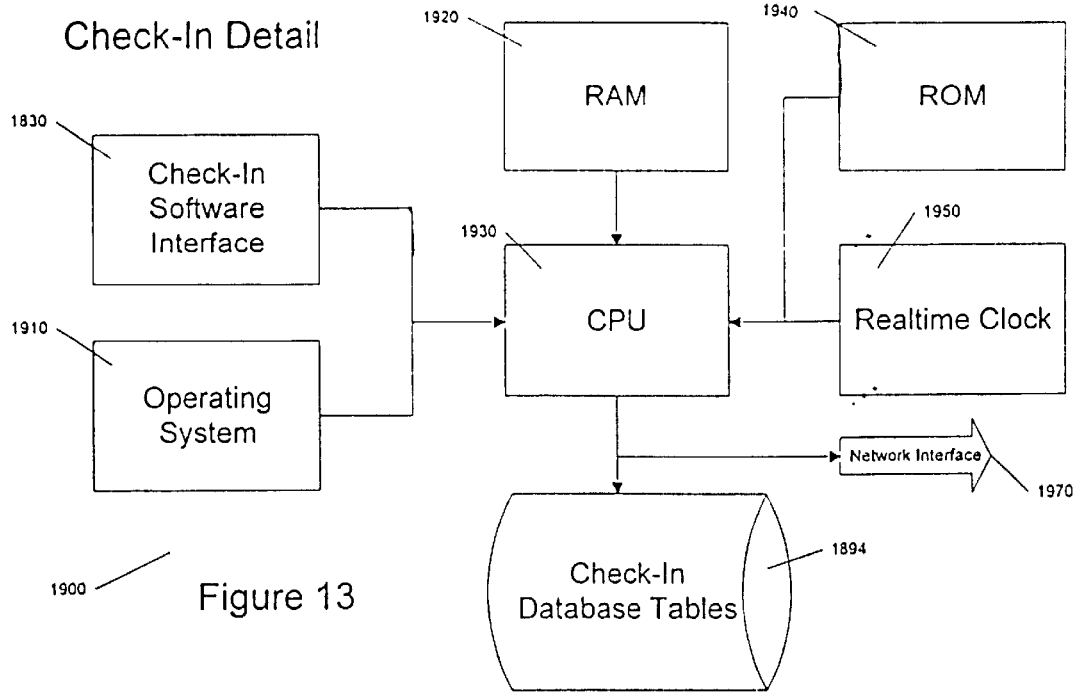

FIG. 13 illustrates the system computer and computer program components for the check-in data entry or personal computer station.

Figure 14:
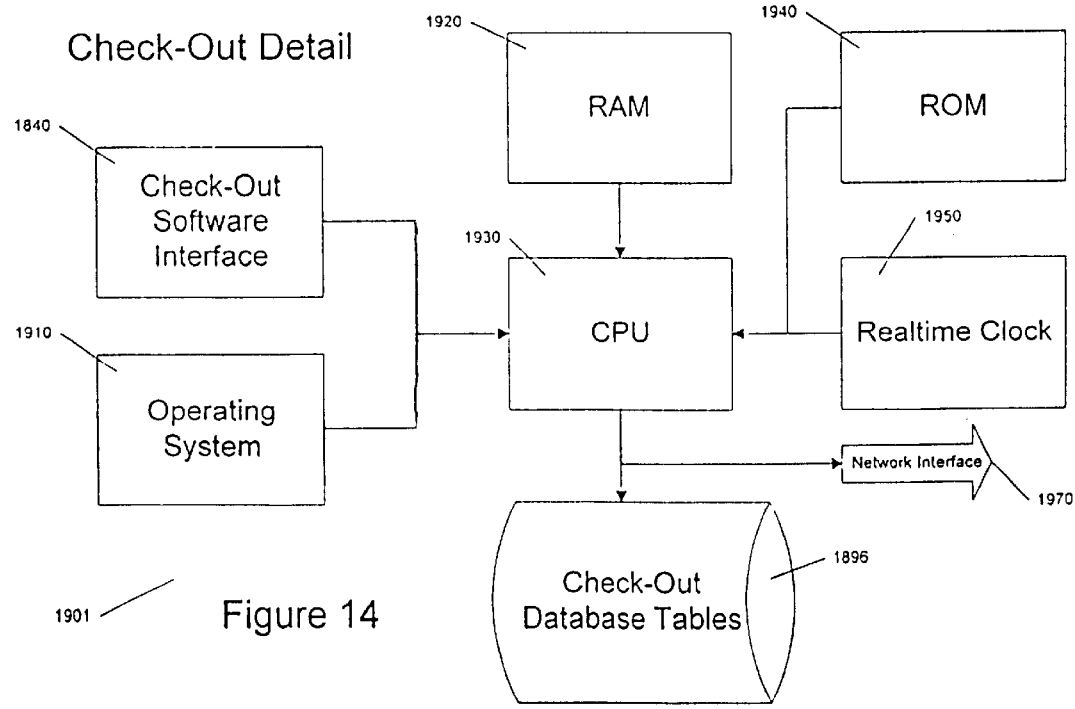

FIG. 14 illustrates the check-out data entry or personal computer station.

Figure 15:
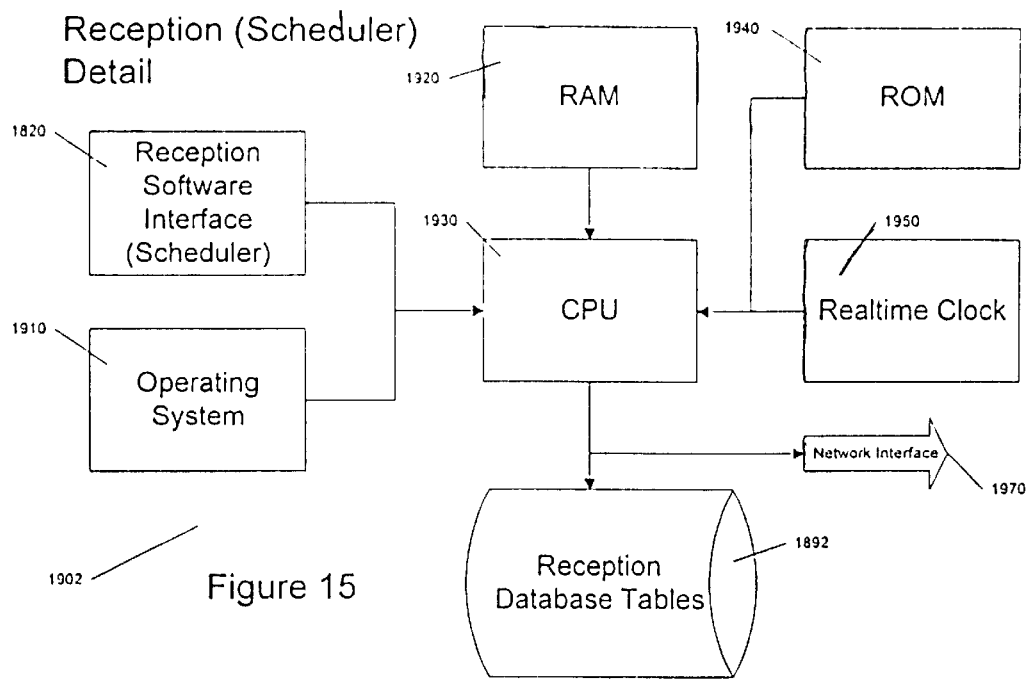

FIG. 15 illustrates the reception/scheduler data entry or personal computer station.

Figure 16:
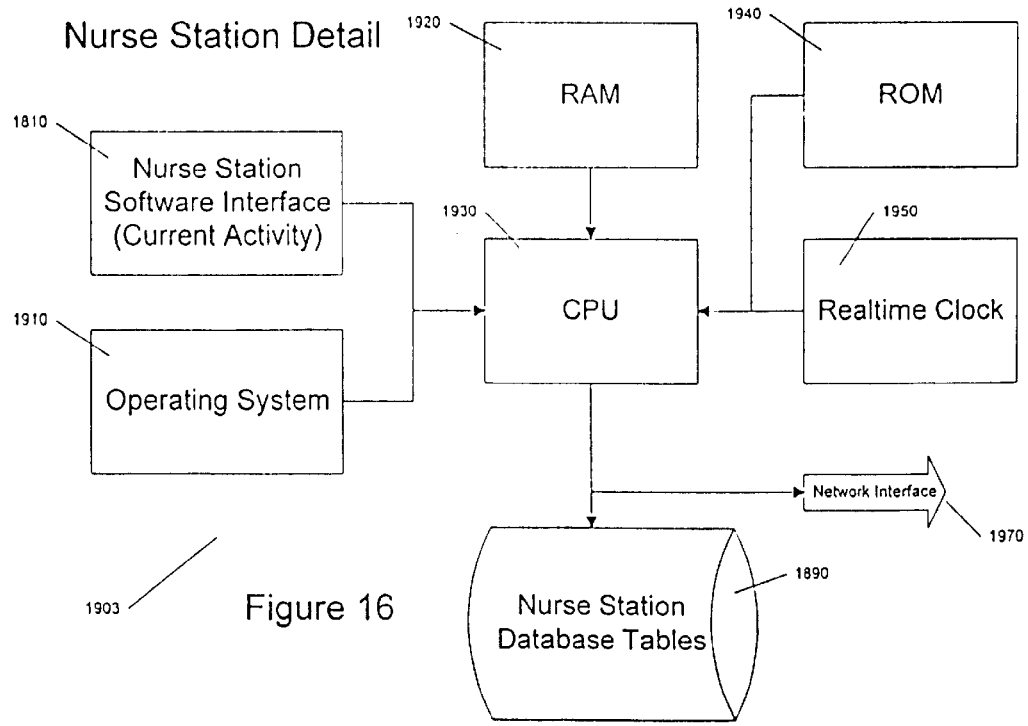

FIG. 16 illustrates the nurse station data entry or personal computer station.

Figure 17:
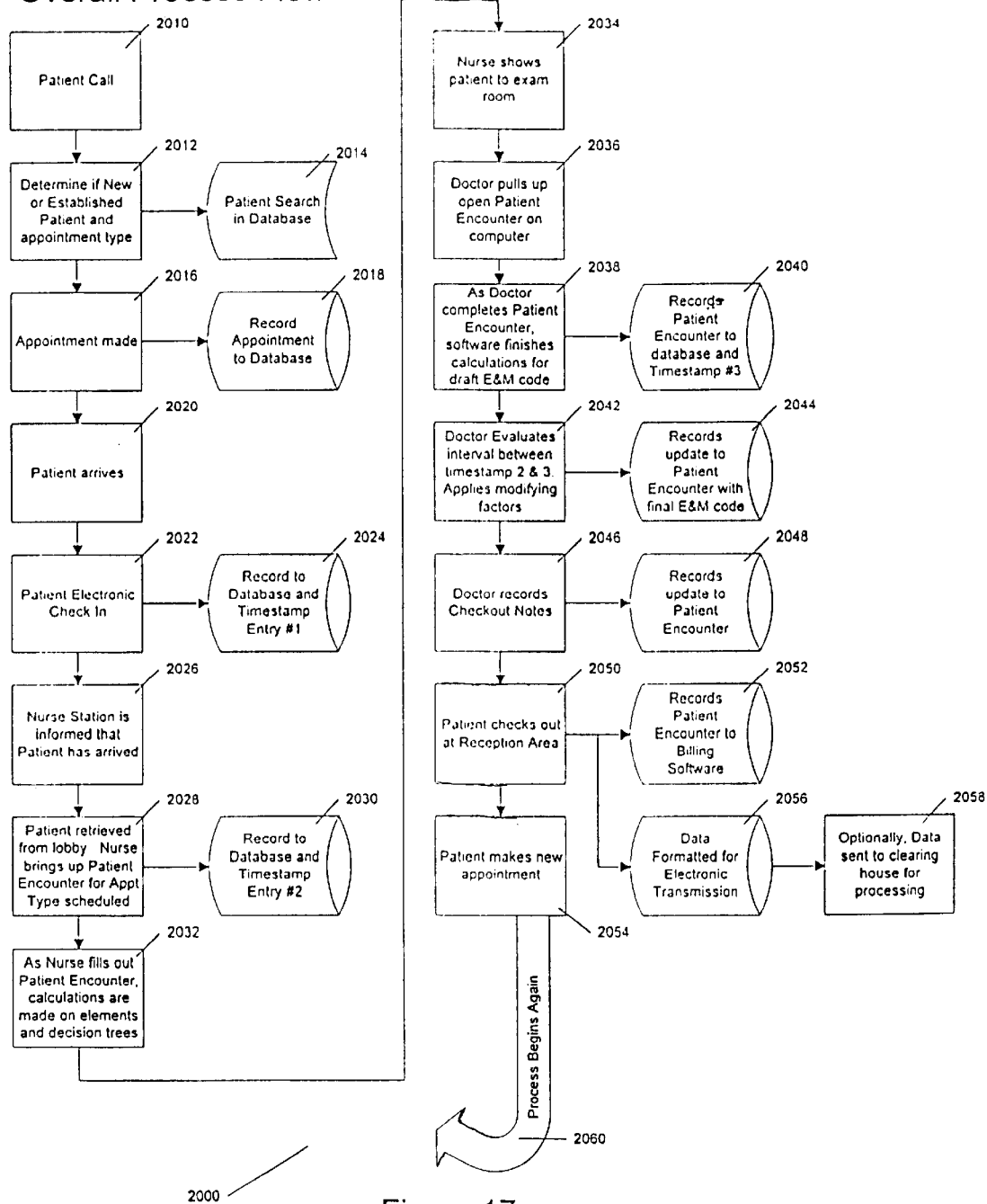

FIG. 17 illustrates the process of the patient encounter resulting in an E&M coding responsive to statutory and regulatory requirements from the patient call for an appointment through data output in the form of an E&M coding, for the provider's use in billing for services or optionally for data transmission to clearing house for processing.

DETAILED DESCRIPTION

The preferred embodiment electronic template medical record coding system disclosed herein is illustrated in FIGS. 1 through 11 and can be provided in software for single-user operation on stand-alone personal computers, for example, by a sole practitioner or for multi-user operations on a network, used for example, by physicians and others within a single facility, clinic, group practice, hospital or other medical providers or organizations. In the preferred embodiment the present invention includes a Central Processing Unit Database server(CPU Database Server) 1870, one or more interfaces.

The system architecture is illustrated with reference to FIGS. 12 through 16, including, for example, Nurse Station Software Interface 1810, Reception Interface 1820, Check-In Interface 1830, Check-Out Interface 1840, Provider Interface 1850, AutoCoder Processor 1860, Database 1880 providing Nurse Station Tables 1890, Reception Tables 1892, Check-In Tables 1894, Check-Out Tables 1896, Provider Tables 1898 and other tables. In the preferred embodiment each of the Nurse Station Software Interface 1810, Reception Interface 1820, Check-In Interface 1830, Check-Out Interface 1840, Provider Interface 1850 have an Operating System 1910, RAM 1920, CPU 1930, ROM 1940 Realtime Clock 1950 and Network Interface 1970. Those of ordinary skill with computer systems and hardware will recognize that different configurations may be envisioned and employed which will be equivalent to that demonstrated in the accompanying figures.

The present invention will have data input from one or more interfaces. The preferred embodiment of the invention will receive data input from the Nurse Station Software Interface 1810, Reception Interface 1820, Check-In Interface 1830, Check-Out Interface 1840 and Provider Interface 1850, as deemed required by the provider, and the computer program to require the computer to manipulate the acquired data to perform realtime audits, during the patient encounter, and to produce an E&M code at the conclusion of the patient encounter. Realtime audits are audits occurring upon the inputting of acquired data, into the computer, following the conclusion of data inputting pertinent to each component of the patient encounter. The provider is prompted to contrast the data actually acquired with that required for the specific type of patient encounter and as required by regulation for billing purposes. The provider thus confirms that requisite data inputting has occurred. In alternative embodiments data may be not be acquired and inputted from one or more of these interfaces. Additionally, those of ordinary skill will recognize that as medical science advances and statutory and regulatory regimes change that other data may be required, for delivery of medical care and the meeting of regulatory requirements; as such changes occur other data will be acquired and inputted with these changes perhaps necessitating interfaces in addition to those noted herein.

Cryptographic processing may be employed where output communications, of final E&M coding or other information, is transmitted, for example via internet or other electronic means, from the provider computer system to entities responsible for reimbursement, auditing or other functions. Conventional personal computer or computer workstations with sufficient memory and processing capability may be used for Nurse Station Software Interface 1810, Reception Interface 1820, Check-In Interface 1830, Check-Out Interface 1840 and Provider Interface 1850 and CPU Database Server 1870. Database 1880 comprises data storage and may include hard disk magnetic or optical storage units as well as CD-ROM drives or flash memory and other means of data storage recognized. Database 1880, including Nurse Station Tables 1890, Reception Tables 1892, Check-In Tables 1894, Check-Out Tables 1896, Provider Tables 1898 and other tables, comprises the databases used in the processing of calculations or transactions in the present invention. In a preferred embodiment, database software is used to create and manage these databases.

Reception Interface 1820 represents immediate interactions with a patient with that interaction resulting in data acquisition which is maintained in the reception data base, Reception Tables 1892(which tracks patient appointments, inquiries, and communications from the provider's workplace with the patient); similarly patient or patient encounter interactions at Nurse Station Software Interface 1810, Check-In Interface 1830, Check-Out Interface 1840 and Provider Interface 1850 represent interactions with a patient with that interaction resulting in data acquisition maintained in the respective data bases Nurse Station Tables 1890 (tracking information taken by a nurse from or regarding a patient or patient encounter), Check-In Tables 1894(tracking the history and patients current status at the time of check-in and the time and date of check-in), Check-Out Tables 1896(tracking the delivery of instructions for laboratory or other care to be sought by the patient and the time and date of check-out), Provider Tables 1898(tracking the History, Physical, Medical Decision Making, and Apply Modifying Variables 1100, 1200, 1300, 1660 leading to the Final E&M Code 1701) and other tables.

Network Interface 1970 is the gateway to communication among Nurse Station Software Interface 1810, Reception Interface 1820, Check-In Interface 1830, Check-Out Interface 1840, Provider Interface 1850 and other interfaces which may be required or added by those of ordinary skill. Conventional network cards or internal or external modems may serve as Network Interface 1970. In a preferred embodiment Network Interface 1970 is connected with workstations at a particular provider site. In an alternative embodiment, Network Interface 1970 may be connected with the internet or a commercial on-line internet service provider. One or more interfaces may be located at remote locations with the Provider Interface 1850 thus having communication capabilities with all other interfaces as required for Final E&M Code 1701. Secure server-based electronic mail software linking people and information over enterprise networks, the internet and other networks, may be employed. Stations providing data are envisioned to be able to exchange messages with enclosures such as files, graphics, video and audio. Additionally, Network Interface 1970, may be configured as a voice mail interface, web site, or electronic mail address. Data acquisition, necessary for the determination of a Final E&M Code 1701, may be acquired from numerous sites and sources, as will be recognized by those of ordinary skill in providing medical services and determining appropriate E&M coding as required by statutory and regulatory agencies.

The principal object of the system's present disclosure is to provide the medical provider, whether individual or organization, with a method and computer hardware/computer program apparatus which insures compliance with coding requirements, of services and health care provided, preliminary to and for billing and reimbursement. An additional object of the method and apparatus disclosed is the electronic and computer automation of the coding process which reduces the potential for human error in coding thereby increasing the likelihood that the coding resulting for each provider/patient encounter will meet regulatory compliance requirements. Another objective of the method disclosed is the greater ease in or realtime production of audit information both for quality control of billings forwarded for reimbursement and for eventual use in the event of an inquiry by an agency.

The prior art coding process shown in FIG. 1 demonstrates the process of developing the History Component 1100, Physical Component 1200 and Medical Decision Component, performing the Prior Art Auditing Process 1030 and establishing, by a manual process, the Final E&M Code 1701.

The preferred embodiment of the present disclosure is illustrated in FIGS. 2 through 7 and 9 through 11 where an electronic template, depending upon the Patient Encounter Category, is chosen at Selection of Template 1050. The provider then gathers and inputs data as required. The method is outlined as follows: A method for using a computer to facilitate E&M coding by a medical provider of a patient encounter comprising: inputting into the computer a code selecting an electronic template specific to a type of patient encounter; acquiring data prompted by the electronic template for the specific type of patient encounter for a specific patient encounter; inputting into the computer the data acquired for the specific type of patient encounter for the specific patient encounter; outputting an audit of the inputted data acquired for the specific patient encounter; inputting into the computer modifying variables for the specific patient encounter; outputting a Final E&M code. The Final E&M code, used for billing purposes will have been subjected to realtime audits as the provider acquires and inputs required data.

The inputting into the computer of a code selecting an electronic template specific to a type of patient encounter comprises inputting into the computer a set of electronic templates, comprising an electronic template for each type of patient encounter, and an electronic template menu; requesting the electronic template menu; selecting by key stroke, mouse, touch pad or other menu selection means, the electronic template specific to the type of patient encounter. The acquiring of data prompted by the electronic template for the specific type of patient encounter comprises examining at least one aspect of the patient encounter, by one or a plurality of patient encounter entities, as prompted by the selected electronic template. The inputting into the computer the data acquired for the specific type of patient encounter for the specific patient encounter comprises inputting into the computer data acquired from the examination of the at least one aspect of the patient encounter. The outputting an audit of the inputted data acquired for the specific patient encounter comprises displaying and comparing the data inputted into the computer with the data required to be acquired, in examining at least one aspect of the patient encounter, as prompted by the selected electronic template and requiring the inputting of an acknowledgment of complete data acquisition and data inputting for the at least one aspect of the patient encounter. The outputting a Preliminary E&M code comprises displaying the data inputted into the computer and requiring the inputting of an acknowledgment of complete data acquisition and data inputting. The inputting into the computer modifying variables for the specific patient encounter comprises identifying the modifying variables pertinent to the specific type of patient encounter; identifying the modifying variables pertinent to the specific patient encounter; selecting the modifying variables pertinent to the specific patient encounter; inputting data representing the selected modifying variables into the computer. The outputting a Final E&M code comprises displaying the data inputted into the computer, requiring the inputting of an acknowledgment of complete data acquisition and data inputting and storing by means the Final E&M code.

The one or a plurality of patient encounter entities includes nurse station software interface, reception interface, check-in interface, check-out interface and provider interface. Patient encounter interactions documented at these stations includes but is not limited to the taking of blood pressure, temperature and weight, the making of an appointment, checking the patient into the office for the appointment, checking the patient out of the office following an appointment, and the many different interactions provided by the licensed medical provider.

The selection of the electronic template includes but is not limited to templates from the group electronic templates for types of patient encounters including general multi-system examination; cardiovascular examination; ear, nose and throat examination; eye examination; genitourinary examination; hematologic/lymphatic/immunologic examination; musculoskeletal examination, neurological examination; psychiatric examination; respiratory examination; and skin examination.

An apparatus for facilitating E&M coding by a medical provider of a patient encounter comprises a storage device, a processor connected to the storage device with the storage device storing a program for controlling the processor. The processor will be operative with the program to receive a code to select an electronic template specific to a type of patient encounter; receive data acquired for the specific type of patient encounter for the specific patient encounter; produce an audit of the data acquired for the specific patient encounter; produce a Preliminary E&M code; receive modifying variables for the specific patient encounter; and produce a Final E&M code.

The apparatus in which the processor is operative with the program will receive a set of electronic templates, comprising an electronic template for each type of patient encounter; produce an electronic template menu; display the electronic template menu upon selection by key stroke, mouse, touch pad or other menu selection means; and display the electronic template specific to the type of patient encounter upon selection; prompt the acquisition of data, by one or a plurality of patient encounter entities, for the specific type of patient encounter for a specific patient encounter; receive data acquired for the specific type of patient encounter for at least one aspect of the patient encounter; conduct an audit by the display and comparison of the data received with the data required to be acquired, in examining at least one aspect of the patient encounter, as prompted by the selected electronic template and require the acknowledgment of complete data acquisition and data receipt for the at least one aspect of the patient encounter; produce a Preliminary E&M code by display of the data and require an acknowledgment of complete data acquisition and data inputting; identify modifying variables pertinent to the specific type of patient encounter; identify the modifying variables pertinent to the specific patient encounter; select the modifying variables pertinent to the specific patient encounter; receive data representing the selected modifying variables; display the data received, require the acknowledgment of complete data acquisition and data inputting, produce the Final E&M code and store the Final E&M code.

The term "electronic" used herein encompasses technologies including electronic, optical and other means of transmitting and manipulating data, instructions and computing devices.

The apparatus in which the processor is operative with the program may select the electronic template from the group of electronic templates for types of patient encounters including general multi-system examination; cardiovascular examination; ear, nose and throat examination; eye examination; genitourinary examination; hematologic/lymphatic/immunologic examination; musculoskeletal examination, neurological examination; psychiatric examination; respiratory examination; and skin examination. Additional templates may be custom made by the provider. The list here made is suggestive only and does not limit templates which may be utilized.

An alternative embodiment of a method for using a computer to facilitate E&M coding by a medical provider of a patient encounter comprises: inputting into the computer a code selecting one or a plurality of electronic template specific to one or a plurality of types of patient encounters; acquiring data prompted by the one or a plurality of electronic templates for the specific one or a plurality of types of patient encounter for a specific patient encounter; inputting into the computer the data acquired for the one or a plurality of specific types of patient encounter for the specific patient encounter; outputting one or a plurality of audits of the inputted data acquired for the specific patient encounter; outputting one or a plurality of Preliminary E&M codes; inputting into the computer one or a plurality of modifying variables for the specific patient encounter; outputting one or a plurality of Final E&M codes.

An alternative embodiment may also include the following: the step of inputting into the computer a code selecting one or a plurality of electronic templates specific to one or a plurality of types of patient encounters may comprise inputting into the computer a set of electronic templates, comprising an electronic template for each type of patient encounter, and an electronic template menu; requesting the electronic template menu; selecting by key stroke, mouse, touch pad or other menu selection means, one or a plurality of electronic template specific to the type of patient encounter. The step of acquiring data prompted by the one or a plurality of electronic templates for the one or a plurality of specific type of patient encounter may comprise examining at least one aspect of the patient encounter, by one or a plurality of patient encounter entities, as prompted by the one or a plurality of the selected electronic templates. The step of inputting into the computer the data acquired for the one or a plurality of specific types of patient encounter for the specific patient encounter may comprise inputting into the computer data acquired from the examination of the at least one aspect of the patient encounter. The step of outputting one or a plurality of audits of the inputted data acquired for the specific patient encounter may comprise displaying and comparing the data inputted into the computer with the data required to be acquired, in examining at least one aspect of the patient encounter, as prompted by the selected one or a plurality of electronic templates and requiring the inputting of one or a plurality of acknowledgments of complete data acquisition and data inputting for the at least one aspect of the patient encounter. The step of outputting one or a plurality of Preliminary E&M codes may comprise displaying the data inputted into the computer and requiring the inputting of one or a plurality of acknowledgments of complete data acquisition and data inputting. The step of inputting into the computer one or a plurality of modifying variables for the specific patient encounter may comprise identifying the one or a plurality of modifying variables pertinent to the one or a plurality of specific types of patient encounter; identifying the one or a plurality of modifying variables pertinent to the specific patient encounter; selecting the one or a plurality of modifying variables pertinent to the specific patient encounter; inputting data representing the selected one or a plurality of modifying variables into the computer. The step of outputting one or a plurality of Final E&M codes may comprise displaying the data inputted into the computer, requiring the inputting of one or a plurality of acknowledgments of complete data acquisition and data inputting, storing by means, the one or a plurality of Final E&M codes.

Alternative embodiments of an apparatus for facilitating E&M coding by a medical provider of a patient encounter comprises the following: a storage device, a processor connected to the storage device where the storage device stores a program for controlling the processor. The processor is operative with the program to receive a code to select an electronic template specific to a type of patient encounter; receive data input acquired for the specific type of patient encounter for the specific patient encounter; output an audit of the data acquired for the specific patient encounter; output a Preliminary E&M code; receive modifying variables for the specific patient encounter; output a Final E&M code; and transmit the Final E&M code. The processor is further operative with the program to receive a set of electronic templates, comprising an electronic template for each type of patient encounter; produce an electronic template menu; display the electronic template menu upon selection by key stroke, mouse, touch pad or other menu selection means; and display the electronic template specific to the type of patient encounter upon selection; prompt the acquisition of data, by one or a plurality of patient encounter entities, for the specific type of patient encounter for a specific patient encounter; receive data acquired for the specific type of patient encounter for at least one aspect of the patient encounter; conduct an audit by the display and comparison of the data received with the data required to be acquired, in examining at least one aspect of the patient encounter, as prompted by the selected electronic template and require the acknowledgment of complete data acquisition and data receipt for the at least one aspect of the patient encounter; produce a Preliminary E&M code by display of the data and require an acknowledgment of complete data acquisition and data inputting; identify modifying variables pertinent to the specific type of patient encounter; identify the modifying variables pertinent to the specific patient encounter; select the modifying variables pertinent to the specific patient encounter; receive data representing the selected modifying variables; display the data received, require the acknowledgment of complete data acquisition and data inputting, produce the Final E&M code and store the Final E&M code. An alternative embodiment of the apparatus is further operative with the program to receive data from one or a plurality of patient encounter entities.

A more detailed description of the preferred method includes the step of acquiring data prompted by the electronic template for the specific type of patient encounter comprising conducting an examination of at least a history component, a physical component and a medical decision component, by one or a plurality of patient encounter entities, as prompted by the selected electronic template. The step of inputting into the computer the data acquired for the specific type of patient encounter for the specific patient encounter comprises inputting into the computer data acquired from the examination of the at least a history component, a physical component and a medical decision component for the patient encounter. The step of outputting an audit of the inputted data acquired for the specific patient encounter comprises displaying and comparing the data inputted into the computer with the data required to be acquired, for the at least a history component, a physical component and a medical decision component for the patient encounter, as prompted by the selected electronic template and requiring the inputting of an acknowledgment of complete data acquisition and data inputting for the at least a history component, a physical component and a medical decision component of the patient encounter. The method includes the outputting a Preliminary E&M code, inputting modifying variables and outputting a Final E&M code.

Figure 3:
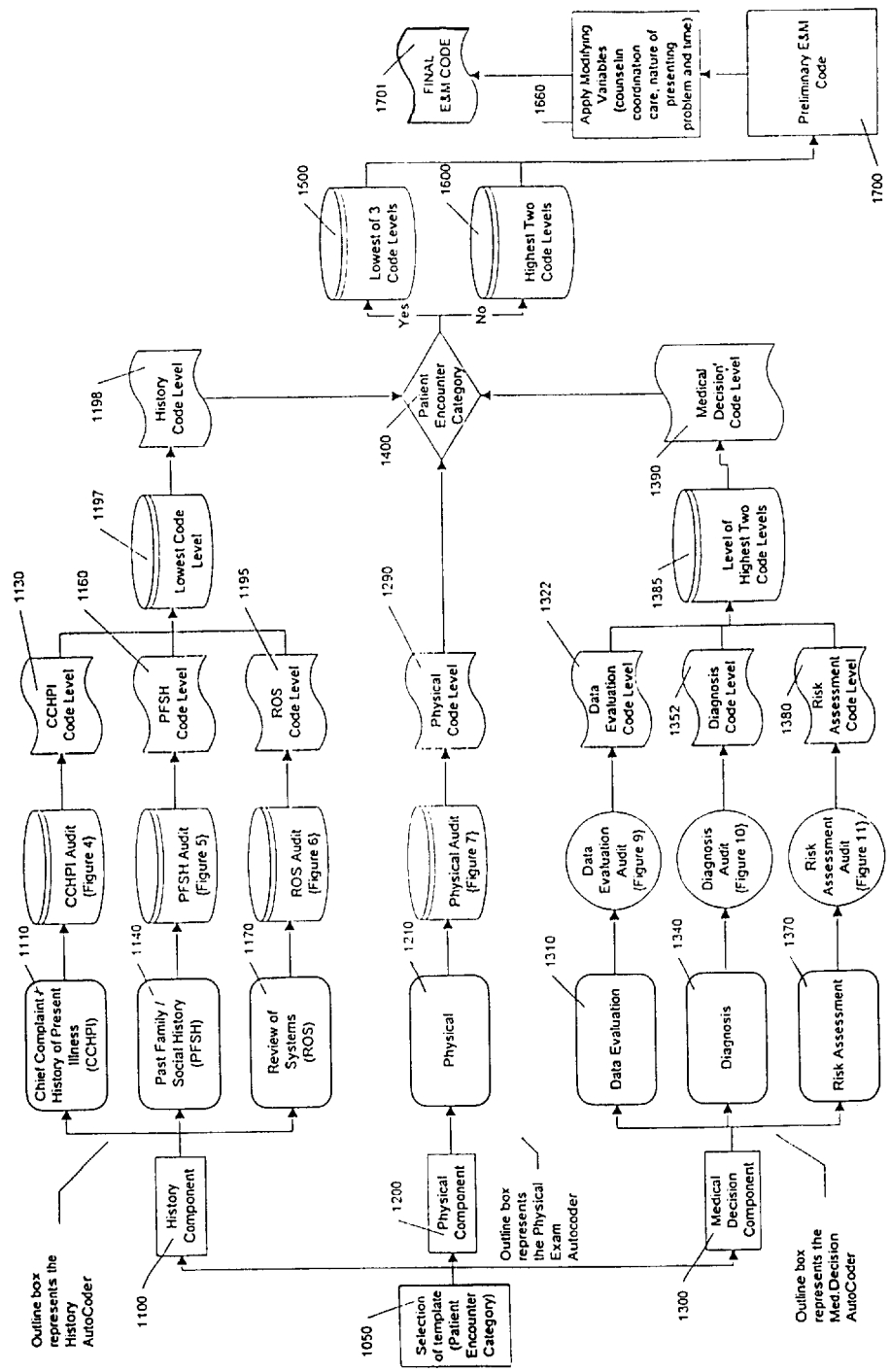
FIG. 3 illustrates the Selection of Template, History Component, Physical Component and Medical Decision Component and associated data entry and computer pre-billing audit process resulting in the computer generation of an E&M Code. The History Component encompasses the provider's data gathering required for CCHPI, PFSH and ROS, the CCHPI, PFSH and ROS Audit following data entry, progresses through the computer generated E&M Code for each of CCHPI Code Level, PFSH Code Level and ROS Code Level to the computer manipulation of each code level to produce the Lowest Code Level. Following is the computer manipulation to produce the History Code Level. The Physical Component encompasses the provider gathering data via the Physical, the Physical Audit following data entry, progresses through the computer generated E&M Code for the Physical Code Level.

With reference to FIGS. 2 and 3 the method is seen to require the step of acquiring data prompted by the electronic template for the at least a history component which comprises taking, at a patient encounter, the Chief Complaint/ History of Present Illness(CCHPI); taking the Past Family Social History(PFSH) and making a Review of Systems (ROS); the step of acquiring data prompted by the electronic template for the at least a physical component which comprises conducting a physical exam; and the step of acquiring data prompted by the electronic template for the at least a medical decision component which comprises making a data evaluation; making a diagnosis; making a risk assessment. Further steps include the step of inputting into the computer the data acquired from the examination of the at least a history component comprising inputting the data of the taking of the CCHPI; inputting the data of the taking of the PFSH, inputting the data of the making of the ROS; the step of inputting into the computer the data acquired from the examination of the at least a physical component comprising inputting the data of the making of the physical exam; the step of inputting into the computer the data acquired the examination of the at least a medical decision component comprising inputting the data from making the data evaluation; inputting the data from making the diagnosis; inputting the data from making the risk assessment; the step of outputting an audit of the data for the at least a history component comprising displaying and comparing the data inputted into the computer with the data required to be acquired as prompted by the selected electronic template, for the at least a history component from the taking of the CCHPI; for the taking of the PFSH; and for the making of the ROS; requiring the inputting of an acknowledgment of complete data acquisition and data inputting for the taking of the CCHPI producing a CCHPI Code Level; for the taking of the PFSH producing a PFSH Code Level; and for the making of the ROS producing a ROS Code Level; the step of outputting an audit of the data for the at least a physical component comprising displaying and comparing the data inputted into the computer with the data required to be acquired as prompted by the selected electronic template, for the at least a physical component from the making of the physical exam; requiring the inputting of an acknowledgment of complete data acquisition and data inputting for the making of the physical exam producing a physical code level; the step of outputting an audit of the data for the at least a medical decision component comprising displaying and comparing the data inputted into the computer with the data required to be acquired as prompted by the selected electronic template, for the at least a medical decision component from the making of the data evaluation; from the making of the diagnosis, and from the making of the risk assessment; requiring the inputting of an acknowledgment of complete data acquisition and data inputting for the making of the data evaluation producing a data evaluation code level, for the making of the diagnosis producing a diagnosis code level, and the making of the risk assessment producing a risk assessment code level; from the making of the physical exam producing a physical code level; the step of outputting a Preliminary E&M code comprising combining the CCHPI code level, the PFSH code level and the ROS code level producing the Lowest Code Level and the History Code Level; combining the data evaluation code level, the diagnosis code level and the risk assessment code level producing the Level of Highest Two Code Levels and the Medical Decision Code Level; combining the History Code Level, the Physical Code Level and the Medical Decision Code Level producing the Patient Encounter Category; selecting from the Patient Encounter Category the Lowest of 3 Code Levels or the Highest Two Code Levels producing the Preliminary E&M code.

The preferred embodiment and alternative embodiments are additionally described as follows: The provider will be prompted, by the electronic template, to acquire specific data relative to particular inquiries required for ultimate medical decisions and as required by statute and regulation. In particular, the provider will acquire data to fulfill the History Component 1100, shown in FIG. 3, with subcomponents shown in FIGS. 2 through 6 of the Chief Complaint History of Present Illness(CCHPI) 1110, Past Family, Social History (PFSH) 1140 and Review of Systems(ROS) 1170. Upon data entry for each of CCHPI 1110, PFSH 1140 and ROS 1170 there results a computer generated appropriate E&M code level of CCHPI, PFSH and ROS Code Level 1130, 1160, 1195 respectively. The provider then undertakes the Physical or Physical Exam 1210 and enters the gathered data required to fulfill the Physical Component 1200, shown in FIG. 3, resulting in the computer generation of the Physical Code Level 1290.

The provider then addresses the Medical Decision Component 1300. The provider undertakes Data Evaluation 1310: the provider determines the number of diagnostic tests ordered or reviewed, i.e., there may be multiple tests ordered for the particular patient encounter; the tests reviewed may follow a patient encounter upon receipt from a laboratory or may occur at a subsequent patient encounter. The Data Evaluation 1310 requires the assignment of specific points to each test ordered. Points assigned include, for example, ultrasound—one point; if the provider performed the ultrasound—two points; the ordering of an x-ray—one point; the reading of an x-ray report—one point; the reading of an x-ray—two points; the microscopic evaluation for yeast—review assigns one point, microscopic evaluation for yeast by the provider assigns two points; the ordering of the microscopic evaluation for yeast assigns one point; the ordering of records or charts assigns one point; the review of records outside the patient encounter assigns one point; the review of records as a part of a patient encounter assigns 2 points. Upon conclusion of Data Evaluation 1310, shown at FIG. 2, the provider enters the gathered data resulting in the computer generation of the Data Evaluation Code Level 1322. The provider then makes the Diagnosis 1340 and enters the gathered data required for the Diagnosis 1340 resulting in the computer generated appropriate E&M code level for Diagnosis Code Level 1352.

Risk Assessment 1370 is then accomplished with entry of data culminating in the computer generated Risk Assessment Code Level 1380. A Preliminary E&M Code 1700 is then computer generated. The provider then proceeds to Apply modifying variables(Time, problem severity) 1660 concluding with the Final E&M Code 1701.

In the preferred embodiment the History Component 1100 includes data acquisition for CCHPI, PFSH and ROS 1110, 1140 and 1170 as shown in FIGS. 2 through 6. The realtime CCHPI 1110 E&M audit is represented in FIG. 3 by "CCHPI Audit" which is illustrated by FIG. 4 showing the CCHPI 1110 decision tree commencing with the CCHPI Encounter Category 1112 to "Established" or to "New". Where to "Established" the tree proceeds to the CCHPI Count Elements 1115 with a possible "4 or More" or "1 to 3". Where "4 or more" the progression is to Extended(Level 5) 1126; where "1 to 3" the progression is to Brief(Level 3) 1124. The final step is the computer generated CCHPI Code Level 1130. Where to "New" the tree proceeds to the CCHPI Count Elements 1115 with a possible "4 or More" or "1 to 3". Where "4 or more" the progression is to Extended(Level 5) 1120; where "1 to 3" the progression is to Brief(Level 2) 1118. The final step is the computer generated CCHPI Code Level 1130.

The realtime PFSH 1140 E&M audit is represented in FIG. 5 showing the PFSH 1140 decision tree commencing with the PFSH Encounter Category 1144 to "Established" or to "New". Where to "Established" the tree proceeds to the PFSH Count Elements 1142 with a possible "Established 0 Elements(Level 3)" 1156, "Established 1 Element (level 4)" 1152 or "Established 2–3 Elements (Level 5)" 1154. The progression from each of "Established 0 Elements(Level 3)" 1156, "Established 1 Element (level 4)" 1152 or "Established 2–3 Elements (Level 5)" 1154 is to the computer generation of PFSH Code Level 1160. Where to "New" the tree proceeds to the PFSH Count Elements 1142 with a possible "New 0 Elements(Level 2)" 1146, "New 1 Element (level 3)" 1148 or "New 3 Elements (Level 5)" 1150. The progression from each of "New 0 Elements(Level 2)" 1146, "New 1 Element (level 3)" 1148 or "New 3 Elements (Level 5)" 1150 is to the computer generation of PFSH Code Level 1160.

The realtime ROS 1160 E&M audit is represented in FIG. 6 showing the ROS 1160 decision tree commencing with the ROS Encounter Category 1172 to "Established" or to "New". Where to "Established" the tree proceeds to the ROS Count Elements 1174 with a possible "Established 0 Elements(Level 2)" 1183, "Established 1 Element (level 3)" 1184, "Established 2–9 Elements (Level 4)" 1186 or "Established 10+ Elements (Level 5) 1188. The progression from each of "Established 0 Elements(Level 2)" 1183, "Established 1 Element (level 3)" 1184, "Established 2–9 Elements (Level 4)" 1186 or "Established 10+ Elements (Level 5)" 1188 is to the computer generation of ROS Code Level 1195. Where to "New" the tree proceeds to the ROS Count Elements 1174 with a possible "New 0 Elements(Level 1)" 1175, "New 1 Element (level 2)" 1176, "New 2–9 Elements (Level 3)" 1178 or "New 10+ Elements(Level 5)" 1180. The progression from each of "New 0 Elements(Level 1)" 1175, "New 1 Element (level 2)" 1176, "New 2–9 Elements (Level 3)" 1178 or "New 10+ Elements(Level 5)" 1180 is to the computer generation of ROS Code Level 1195.

The output of each of CCHPI Code Level 1130, PFSH Code Level 1160 and ROS Code Level 1195 is interrogated to produce via the decision tree the Lowest Code Level 1197 then establishing the History Code Level 1198.

In the preferred embodiment the Physical Component 1200, shown in FIG. 3, commences with data acquisition via the Physical 1210. The immediately following Physical 1210 E&M audit is represented by FIG. 7 showing the Physical 1210 decision tree commencing with the Organ System Body Area 1212 to "Other" or to "Eye or Psychiatric". Where to "Other" the tree proceeds to the "Physical Patient Encounter Category" 1214 with a possible "Established" or "New". Where "Established" the progression is to "Other Established 1–5 Elements(Level 2)" 1250, "Other Established 6–11 Element (level 3)" 1252, "Other Established 12+ Elements (Level 4)" 1254 or "Physical Decision Matrix (Level 5)" 1226. The progression from each of "Other Established 1–5 Elements(Level 2)" 1250, "Other Established 6–11 Element (level 3)" 1252, "Other Established 12+ Elements (Level 4)" 1254 or "Physical Decision Matrix (Level 5)" 1226 is to the computer generation of Physical Code Level 1290. Where to "Other", "Physical Patient Encounter Category" 1214 and "New" the tree proceeds to the "Other New 1–5 Elements(Level 1)" 1240, "Other New 6–11 Elements (level 2)" 1242, "Other New 12+ Elements (Level 3)" 1244 or "Physical Decision Matrix (Level 5)" 1226. The progression from each of "Other New 1–5 Elements(Level 1)" 1240, "Other New 6–11 Elements (level 2)" 1242, "Other New 12+ Elements (Level 3)" 1244 or "Physical Decision Matrix (Level 5)" 1226 is to the computer generation of Physical Code Level 1290.

Where to "Eye or Psychiatric" the tree proceeds to the "Physical Patient Encounter Category" 1214 with a possible "Established" or "New". Where to "Established" the progression is to the "E or P Established 1–5 Elements(Level 2)" 1230, "E or P Established 6–8 Elements (level 3)" 1232, "E or P Established 9+ Elements (Level 4)" 1234 or "Physical Decision Matrix (Level 5)" 1226. The progression from each of "E or P Established 1–5 Elements(Level 2)" 1230, "E or P Established 6–8 Elements (level 3)" 1232, "E or P Established 9+ Elements (Level 4)" 1234 or "Physical Decision Matrix (Level 5)" 1226 is to the computer generation of Physical Code Level 1290.

Where to "Eye or Psychiatric", "Physical Patient Encounter Category" 1214 and "New" the tree proceeds to the "E or P New 1–5 Elements(Level 1)" 1220, "E or P New 6–8 Elements (level 2)" 1222, "E or P New 9+ Elements (Level 3)" 1224 or "Physical Decision Matrix (Level 5)" 1226. The progression from each of "E or P New 1–5 Elements(Level 1)" 1220, "E or P New 6–8 Elements (level 2)" 1222, "E or P New 9+ Elements (Level 3)" 1224 or "Physical Decision Matrix (Level 5)" 1226 is to the computer generation of Physical Code Level 1290.

In the preferred embodiment the provider undertakes data acquisition for the Medical Decision Component 1300, shown in FIG. 3 with subcomponents shown in FIGS. 2, 3 and 9 through 11 of Data Evaluation 1310, Diagnosis 1340 and Risk Assessment 1370. FIG. 9 shows the Data Evaluation 1310 decision tree commencing with the "Data Evaluation Audit" 1311 proceeding to the choices of "Data Minimal=0 to 1 Point(Level 2)" 1314, "Data Limited=2 Points (Level 3)" 1316, "Data Moderate=3 Points (Level 3 New Patient, Level 4 Est. Patient)" 1318 or, "Data Extensive=4 or more Points (Level 5)" 1320. The progression from each of "Data Minimal=0 to 1 Point(Level 2)" 1314, "Data Limited=2 Points (Level 3)" 1346, "Data Moderate=3 Points (Level 3 New Patient, Level 4 Est. Patient)" 1318 or, "Data Extensive=4 or more Points (Level 5)" 1320 is to the computer generation of Data Evaluation Code Level 1322.

FIG. 10 shows the Diagnosis 1340 decision tree commencing with the "Diagnosis Audit" 1342 proceeding to the choices of "Diagnosis Minimal=1 Point(Level 2)" 1344, "Diagnosis Limited=2 Points (Level 3)" 1346, "Diagnosis Multiple=3 Points (Level 4)" 1348 or, "Diagnosis Extensive=4 or more Points (Level 5)" 1350. The progression from each of "Diagnosis Audit" 1342 proceeding to the choices of"Diagnosis Minimal=1 Point(Level 2)" 1344, "Diagnosis Limited=2 Points (Level 3)" 1346, "Diagnosis Multiple=3 Points (Level 4)" 1348 or, "Diagnosis Extensive=4 or more Points (Level 5)" 1350 is to the computer generation of Diagnosis Code Level 1352.

FIG. 11 shows the Risk Assessment 1370 decision tree commencing with the analysis of each of "Presenting Problem" 1372, "Diagnostic Procedure(s) Ordered" 1374, and "Managed Options Selected" 1376 with the following computer examination for the Highest Level of Risk Assessment 1378 and progressing to the computer determination of the Risk Assessment Code Level 1380.

FIGS. 12 through 16 are illustrative of embodiments of system interfaces for the introduction of data. Data may be introduced or inputted by at least one or by one or plurality of patient encounter entities. FIG. 12 is illustrative of patient encounter entities or system interfaces 1800 including nurse station software interface 1810, reception interface 1820, check-in interface 1830, check-out interface 1840, provider interface 1850, autocoder processor 1860, CPU database server 1870, database 1880, nurse station tables 1890, reception tables 1892, check in tables 1894, checkout tables 1896, provider(patient encounter) tables 1898.

FIG. 13 illustrates the check-in interface 1900. FIG. 14 is illustrative of the check-out interface 1901. FIG. 15 illustrates the reception(scheduler) interface 1902. FIG. 16 illustrates the Nurse Station Interface 1903.

FIG. 17 is demonstrative of the E&M coding process 2000 from patient call 2010 through the production of a final E&M code 2044 and continuing to the concluding act of the provider in providing care and in managing E&M coding.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for using a computer to facilitate E&M coding by a medical provider of a patient encounter comprising:
   A. inputting into the computer a code selecting An electronic template specific to a type of patient encounter;
   B. acquiring data prompted by the electronic template for the specific type of patient encounter for a specific patient encounter;
   C. inputting into the computer the data acquired for the specific type of patient encounter for the specific patient encounter;
   D. outputting an audit of the inputted data acquired for the specific patient encounter;
   E. outputting a Preliminary E&M code;
   F. inputting into the computer modifying variables for the specific patient encounter;
   G. outputting a Final E&M code;

the method in which the step of inputting into the computer a code selecting an electronic template specific to a type of patient encounter further comprises:
   H. inputting into the computer a set of electronic templates and an electronic template menu;

and in which the step of acquiring data prompted by the electronic template for the specific type of patient encounter comprises:
   I. examining at least one aspect of the patient encounter, and in which the step of inputting into the computer the data acquired for the specific type of patient encounter for the specific patient encounter comprises:
   J. inputting into the computer data acquired from the examination of the at least one aspect of the patient encounter;

and in which the step of outputting an audit of the inputted data acquired for the specific patient encounter comprises:
   K. displaying and comparing the data inputted into the computer with the data required to be acquired, in examining at least one aspect of the patient encounter, and in which the step of outputting a Preliminary E&M code comprises:
   L. displaying the data inputted into the computer and requiring the inputting of an acknowledgment of complete data acquisition and data inputting;

and in which the step of inputting into the computer modifying variables for the specific patient encounter comprises;
   M. identifying the modifying variables pertinent to the specific type of patient encounter; identifying the modifying variables pertinent to the specific patient encounter;

and in which the step of outputting a Final E&M code comprises:
   N. displaying the data inputted into the computer, requiring the inputting of an acknowledgment of complete data acquisition and data inputting, storing by means, the Final E&M code.

2. The method of claim 1 further comprising:
   A. the set of electronic templates comprising an electronic template for each type of patient encounter; requesting the electronic template menu; selecting by key stroke, mouse, touch pad or other menu selection means, the electronic template specific to the type of patient encounter;
   B. examining at the at least one aspect of the patient encounter, by one or a plurality of patient encounter entities, as prompted by the selected electronic template;
   C. displaying aid comparing the data inputted into the computer with the data required to be acquired as prompted by the selected electronic template and requiring the inputting of an acknowledgment of complete data acquisition and data inputting for the at least one aspect of the patient encounter;
   D. displaying the data inputted into the computer and requiring the inputting of an acknowledgment of complete data acquisition and data inputting; and in which the step of inputting into the computer modifying variables for the specific patient encounter comprises;
   E. selecting the modifying variables pertinent to the specific patient encounter; inputting data representing the selected modifying variables into the computer;
   F. displaying the data inputted into the computer, requiring the inputting of an acknowledgment of complete data acquisition and data inputting, storing by means, the Final E&M code.

3. The method of claim 2 in which the one or a plurality of patient encounter entities includes nurse station software interface, reception interface, check-in interface, check-out interface and provider interface.

4. The method of claim 2 in which the selection of the electronic template is from the group electronic templates for types of patient encounters including general multi-system examination; cardiovascular examination; ear, nose and throat examination; eye examination; genitourinary examination; hematologic/lymphatic/immunologic examination; musculoskeletal examination, neurological examination; psychiatric examination; respiratory examination; and skin examination.

5. A method for using a computer to facilitate E&M coding by a medical provider of a patient encounter comprising:

A. inputting into the computer a code selecting one or a plurality of electronic template specific to one or a plurality of types of patient encounters;

B. acquiring data prompted by the one or a plurality of electronic templates for the specific one or a plurality of types of patient encounter for a specific patient encounter;

C inputting into the computer the data acquired for the one or a plurality of specific types of patient encounter for the specific patient encounter;

D. outputting one or a plurality of audits of the inputted data acquired for the specific patient encounter;

E. outputting one or a plurality of Preliminary E&M codes;

F. inputting into the computer one or a plurality of modifying variables for the specific patient encounter;

G. outputting one or a plurality of Final E&M codes;

the method of inputting into the computer a code selecting one or a plurality of electronic templates specific to one or a plurality of types of patient encounters further comprises:

H. inputting into the computer a set of electronic templates and an electronic template menu; requesting the electronic template menu;

and in which the step of acquiring data prompted by the one or a plurality of electronic templates for the one or a plurality of specific type of patient encounter comprises:

I. examining at least one aspect of the patient encounter, and in which the step of inputting into the computer the data acquired for the one or a plurality of specific types of patient encounter for the specific patient encounter comprises:

J. inputting into the computer data acquired from the examination of the at least one aspect of tie patient encounter;

and in which the step of outputting one or a plurality of audits of the inputted data acquired for the specific patient encounter comprises;

K. displaying and comparing the data inputted into the computer with the data required to be acquired, in examining at least one aspect of the patient encounter;

and in which the step of outputting one or a plurality of Preliminary E&M codes comprises:

L. displaying the data inputted into the computer and requiring the inputting of one or a plurality of acknowledgments of complete data acquisition and data inputting;

and in which the step of inputting into the computer one or a plurality of modifying variables for the specific patient encounter comprises;

M. identifying the one or a plurality of modifying variables pertinent to the one or a plurality of specific types of patient encounter; identifying the one or a plurality of modifying variables pertinent to the specific patient encounter;

and in which the step of outputting one or a plurality of Final E&M codes comprises:

N. displaying the data inputted into the computer, requiring the inputting of one or a plurality of acknowledgments of complete data acquisition and data inputting, storing by means, the one or a plurality of Final E&M codes.

6. The method of claim 5 further comprising:

A. inputting into the computer the set of electronic templates comprising an electronic template for each type of patient encounter, selecting by key stroke, mouse, touch pad or other menu selection means, one or a plurality of electronic template specific to the type of patient encounter;

B. examining the at least one aspect of the patient encounter by one or a plurality of patient encounter entities, as prompted by the one or a plurality of the selected electronic templates;

C. displaying and comparing the data inputted into the computer with the data required to be acquired as prompted by the selected one or a plurality of electronic templates and requiring the inputting of one or a plurality of acknowledgments of complete data acquisition and data inputting for the at the least one aspect of the patient encounter;

D. selecting the one or a plurality of modifying variables pertinent to the specific patient encounter; inputting data representing the selected one or a plurality of modifying variables into the computer.

7. The method of claim 6 in which the one or a plurality of patient encounter entities includes nurse station software interface, reception interface, check-in interface, check-out interface and provider interface.

8. The method of claim 6 in which the selection of the one or a plurality of electronic templates is from the group electronic templates for types of patient encounters including general multi-system examination; cardiovascular examination; ear, nose and throat examination; eye examination; genitourinary examination; hematologic/lymphatic/immunologic examination; musculoskeletal examination, neurological examination; psychiatric examination; respiratory examination; and skin examination.

9. The method of claim 6 in which the step of acquiring data prompted by the electronic template for the specific type of patient encounter comprises:

A. conducting an examination of at least a history component, a physical component and a medical decision component, by one or a plurality of patient encounter entities, as prompted by the selected electronic template;

and in which the step of inputting into the computer the data acquired for the specific type of patient encounter for the specific patient encounter comprises:

B. inputting into the computer data acquired from the examination of the at least a history component, a physical component and a medical decision component for the patient encounter;

and in which the step of outputting an audit of the inputted data acquired for the specific patient encounter comprises:

D. displaying and comparing the data inputted into the computer with the data required to be acquired, for the at least a history component, a physical component and a medical decision component for the patient encounter, as prompted by the selected electronic template and requiring the inputting of an acknowledgment of complete data acquisition and data inputting for the at least a history component, a physical component and a medical decision component of the patient encounter;

E. outputting a Preliminary E&M code;

F. inputting modifying variables;

G. outputting a Final E&M code.

10. The method of claim 9 in which the step of acquiring data prompted by the electronic template for the at least a history component comprises:

A. taking, at a patient encounter, the Chief Complaint/History of Present Illness(CCHPI); taking the Past Family Social History(PFSH) and making a Review of Systems(ROS);

and in which the step of acquiring data prompted by the electronic template for the at least a physical component comprises:

B. conducting a physical exam;

and in which the step of acquiring data prompted by the electronic template for the at least a medical decision component comprises:

C. making a data evaluation; making a diagnosis; making a risk assessment;

and in which the step of inputting into the computer the data acquired from the examination of the at least a history component:

D. inputting the data of the taking of the CCHPI; inputting the data of the taking of the PFSH, inputting the data of the making of the ROS;

and in which the step of inputting into the computer the data acquired from the examination of the at least a physical component:

F. inputting the data of the making of the physical exam;

and in which the step of inputting into the computer the data acquired the examination of the at least a medical decision component:

H. inputting the data from making the data evaluation; inputting the data from making the diagnosis; inputting the data from making the risk assessment;

and in which the step of outputting an audit of the data for the at least a history component:

I. displaying and comparing the data inputted into the computer with the data required to be acquired as prompted by the selected electronic template, for the at least a history component from the taking of the CCHPI; for the taking of the PFSH; and for the making of the ROS; requiring the inputting of an acknowledgment of complete data acquisition and data inputting for the taking of the CCHPI producing a CCHPI Code Level; for the taking of the PFSH producing a PFSH Code Level; and for the making of the ROS producing a ROS Code Level;

and in which the step of outputting an audit of the data for the at least a physical component:

J. displaying and comparing the data inputted into the computer with the data required to be acquired as prompted by the selected electronic template, for the at least a physical component from the making of the physical exam; requiring the inputting of an acknowledgment of complete data acquisition and data inputting for the making of the physical exam producing a physical code level;

and in which the step of outputting an audit of the data for the at least a medical decision component:

K. displaying and comparing the data inputted into the computer with the data required to be acquired as prompted by the selected electronic template, for the at least a medical decision component from the making of the data evaluation; from the making of the diagnosis, and from the making of the risk assessment; requiring the inputting of an acknowledgment of complete data acquisition and data inputting for the making of the data evaluation producing a data evaluation code level, for the making of the diagnosis producing a diagnosis code level, and the making of the risk assessment producing a risk assessment code level; from the making of the physical exam producing a physical code level;

and in which the step of outputting a Preliminary E&M code comprises:

L. combining the CCHPI code level, the PFSH code level and the ROS code level producing the Lowest Code Level and the History Code Level; combining the data evaluation code level, the diagnosis code level and the risk assessment code level producing the Level of Highest Two Code Levels and the Medical Decision Code Level; combining the History Code Level, the Physical Code Level and the Medical Decision Code Level producing the Patient Encounter Category; selecting from the Patient Encounter Category the Lowest of 3 Code Levels or the Highest Two Code Levels producing the Preliminary E&M code.

* * * * *